United States Patent [19]

Masuho et al.

[11] Patent Number: 5,783,670

[45] Date of Patent: *Jul. 21, 1998

[54] MONOCLONAL ANTIBODIES SPECIFIC FOR HIV AND THE HYBRIDOMAS FOR PRODUCTION THEREOF

[75] Inventors: Yasuhiko Masuho; Toru Sugano; Yoh-ichi Matsumoto; Takashi Kawamura, all of Tokyo, Japan; Evan Hersh, Tucson, Ariz.; Eskild Petersen, Tucson, Ariz.; Douglas Lake, Tucson, Ariz.

[73] Assignees: The University of Arizona, Department of Internal Medicine, Section of Hematology and Oncology, Tucson, Ariz.; Teijin Limited, Osaka, Japan

[*] Notice: The term of this patent shall not extend beyond the expiration date of Pat. No. 5,695,927.

[21] Appl. No.: 487,529

[22] Filed: Jun. 7, 1995

Related U.S. Application Data

[62] Division of Ser. No. 270,214, Jul. 1, 1994, which is a continuation of Ser. No. 864,540, Apr. 7, 1992, abandoned, which is a continuation-in-part of Ser. No. 342,899, Apr. 25, 1989, abandoned, which is a continuation-in-part of Ser. No. 176,159, Mar. 31, 1988, Pat. No. 5,298,419.

[51] Int. Cl.$^6$ .......................... C07K 16/10; A61K 39/42
[52] U.S. Cl. ..................... 530/388.15; 424/142.1; 424/148.1; 530/388.35
[58] Field of Search ............... 424/148.1, 188.1, 424/208.1, 142.1; 435/5, 7, 24; 530/388.15, 388.35, 388.75, 389.4, 389.6

[56] References Cited

PUBLICATIONS

Fahey et al, "Status of Immune-based Therapies in HIV Infections and AIDS," *Clin. Exp. Immunol.* 88:1–5, 1992.
Fox, J.L., "No Winners Against AIDS," *Bio/Technology* 12:128, Feb. 1994.

*Primary Examiner*—Robert D. Budens
*Attorney, Agent, or Firm*—Oblon, Spivak, McClelland, Maier & Neustadt, P.C.

[57] ABSTRACT

Human monoclonal antibodies which belong to the IgG1 subclass and are specific for HIV are described. The monoclonal antibodies have potential for use in the diagnosis, prevention and therapy of HIV infection.

2 Claims, 12 Drawing Sheets

A: AIDS PATIENT'S SERUM
B: HEALTHY DONOR SERUM
C: NO. 86
D: " SUBCLONE 1.
E: " SUBCLONE 2.
F: " SUBCLONE 3.
G: " SUBCLONE 4.
H: " NO. 1
I: " 81-1

| LANE | |
|---|---|
| 1 | MOLECULAR WEIGHT MARKER USED Ag |
| 2 | MOCK INFECTED Ag |
| 3 | DTT TREATED MOCK INFECTED Ag |
| 4 | HTLVIIIb Ag |
| 5 | DTT TREATED HTLVIIIb Ag |
| 6 | HTLVIIIMN Ag |
| 7 | DTT TREATED HTLVIIIMN Ag |
| 8 | HTLLIIIRF Ag |
| 9 | DTT TREATED HTLVIIIRF Ag |

...... UNINFECTED CELLS
____ HIV-INFECTED CELLS

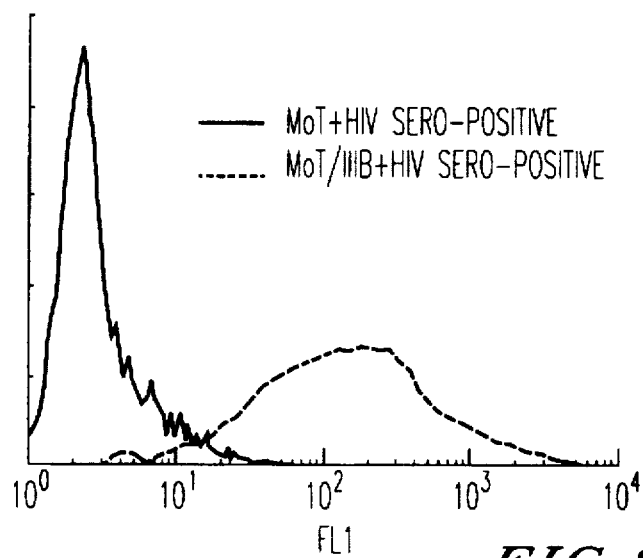
FIG. 9A(i)
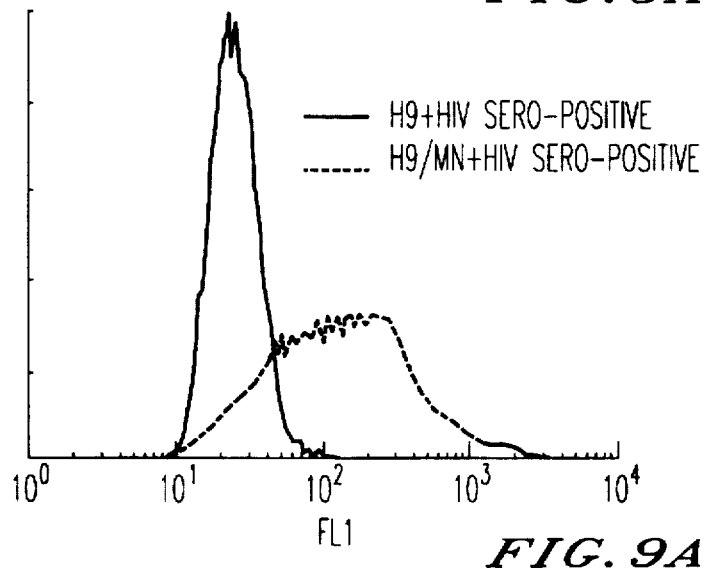
FIG. 9A(ii)
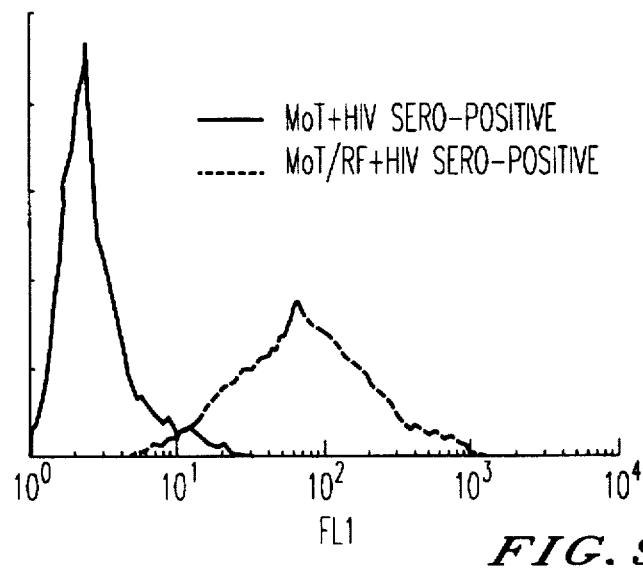
FIG. 9A(iii)

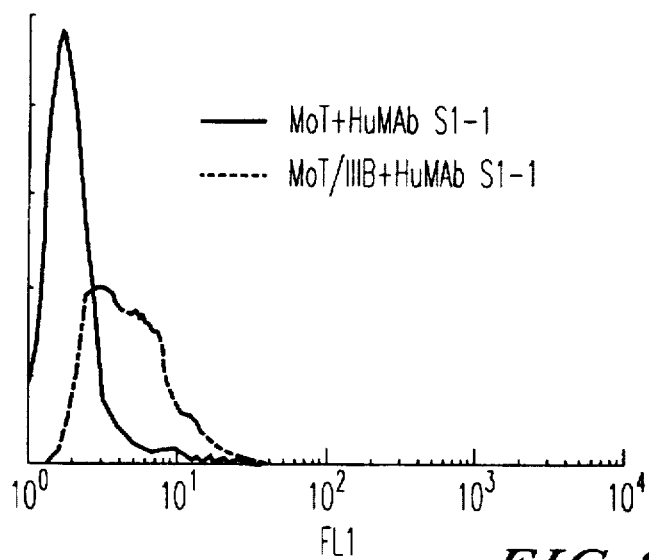
FIG. 9B(i)
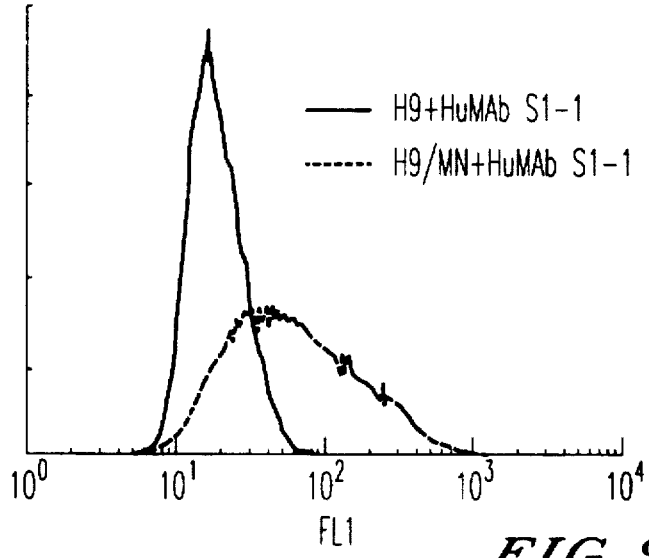
FIG. 9B(ii)
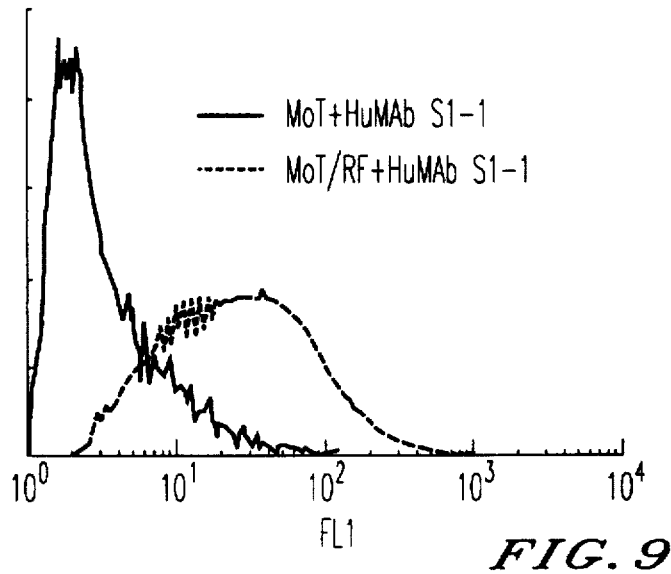
FIG. 9B(iii)

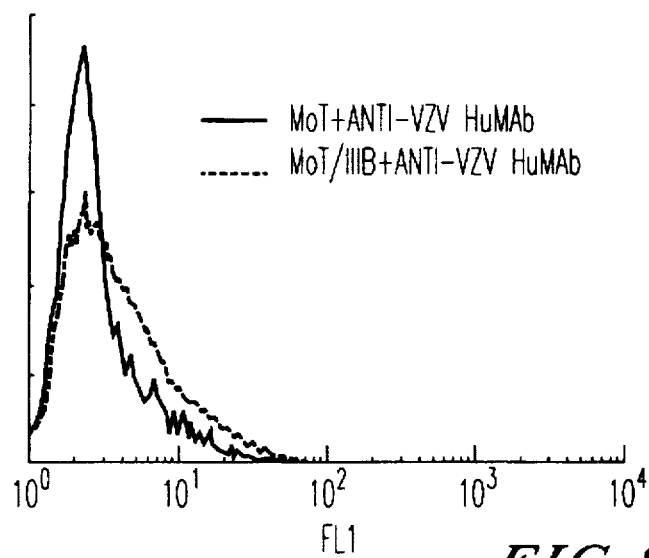
FIG. 9C(i)
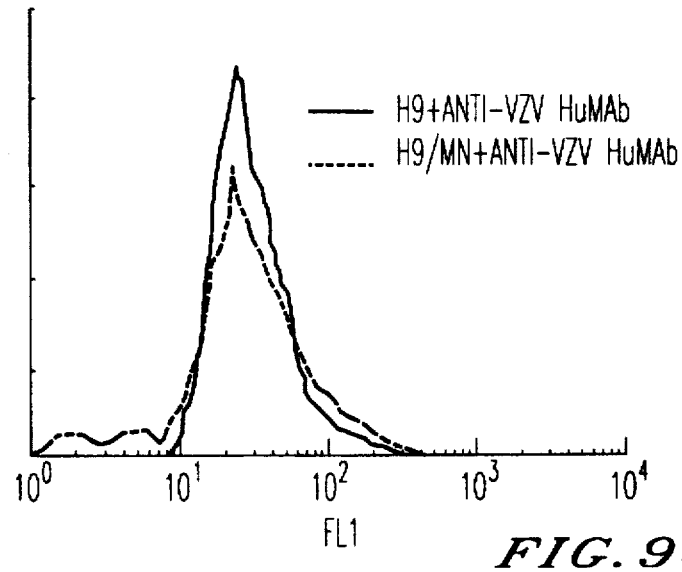
FIG. 9C(ii)
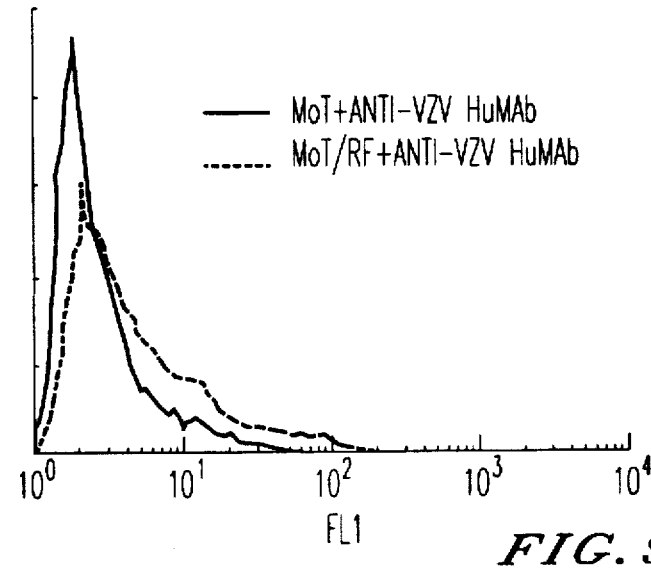
FIG. 9C(iii)

MONOCLONAL ANTIBODIES SPECIFIC FOR HIV AND THE HYBRIDOMAS FOR PRODUCTION THEREOF

This is a Division of application Ser. No. 08/270,214 filed on Jul. 1, 1994, which is a Continuation of application Ser. No. 07/864,540 filed on Apr. 7, 1992, abandoned, which is a Continuation-in-Part of application Ser. No. 07/342,899 filed on Apr. 25, 1989, abandoned, which is a Continuation-in-Part of application Ser. No. 07/176,159 filed on Mar. 31, 1988, which issued as U.S. Pat. No. 5,298,419 on Mar. 29, 1994.

BACKGROUND OF THE INVENTION

1. Field of the Invention

The present invention relates to human monoclonal antibodies (abbreviated as MCAs hereinafter) specific for the human immunodeficiency virus, and the hybridomas which produce the MCAs. The objective of this invention is to provide human MCAs which are specific for HIV and which will be useful in the diagnosis, prevention and therapy of HIV infection.

2. Discussion of the Background

HIV is a virus which primarily infects helper T lymphocytes and brings about extreme immunological failure by destroying those cells, thereby causing AIDS (acquired immunodeficiency syndrome). In the early stage of HIV infection, some patients develop symptoms which resemble those of infectious mononucleosis, i.e., fever, fatigue, headache, etc. Subsequently, although the patient becomes asymptomatic, he/she becomes a carrier of anti-HIV antibodies in the blood. Then, after a latent period lasting a number of years, the patient develops AIDS-related complex (ARC). ARC patients exhibit various symptoms such as systemic swelling of lymph nodes, fever, general fatigue, weight loss, decreased platelet and lymphocyte levels, etc. As the disease progresses, the patient becomes susceptible to and develops Kaposi's sarcoma or malignant lymphoma and various opportunistic infections such as *Pneumocystis carinii* pneumonia, fungal infections, cytomegalovirus infection, etc., which end in death. The most striking characteristics of AIDS are the decrease in helper T lymphocytes (CD4), and a steady decrease in the ratio of CD4 to suppressor T lymphocytes (CD8), i.e., T4/T8, as the disease progresses.

AIDS was first reported in the United States of America in 1981, and it has been estimated that today there are more than 100,000 AIDS patients in the U.S.A. alone. Carriers of the virus have been estimated to number one million persons in the U.S.A. In addition to the U.S.A., there are also many AIDS victims in Africa and Europe, and there is a huge amount of research being carried out today on methods for the diagnosis, prevention and treatment of AIDS.

HIV, the causative agent of AIDS, is a retrovirus. This virus has been shown to be composed of RNA consisting of about 9,700 base pairs, three gag proteins (having molecular weights of 55,000, 24,000 and 17,000 daltons), a reverse transcriptase (molecular weights of 66,000 and 51,000 daltons have been detected), three glycoproteins (two molecules having molecular weights of 120,000 and 41,000 daltons, and their precursor, a molecule with a molecular weight of 160,000 daltons; these glycoproteins are hereinafter abbreviated as gp120, gp41 and gp160) which comprise the envelope, and other components. Especially from the viewpoints of viral infection and the prevention thereof, the envelope, which is exposed as the surface of HIV, carries particular importance. As a result of proteolysis, gp160 is cleaved into gp120 and gp41. Gp41 is a transmembrane protein which is incorporated into the lipid bilayer of the viral envelope, while gp120 is exposed on the outside of the envelope and some of it is released from the virus. Both gp41 and gp120 possess many sugar-binding sites, and about half of the gp120 molecule is comprised of sugars. The gp120 molecule binds to, or near to, the CD4 antigens which exist on the cell surface of helper T cells, etc., and in addition to bringing about infection of the cells by the virus, gp120 possesses activity which results in the syncytium formation in the infected cells. Once HIV is bound to CD4 via gp120, another env gene product, gp41 mediates fusion between the membranes of the cell and the virus allowing the core of the virus to enter the cell.

There is considerable evidence that the presence of neutralizing antibody to HIV in the HIV patient is predictive of a good prognosis. For example, M. Robert-Guroff et al. (J. Immunol. 138: 3731, 1987) reported that the progression of the disease was slower in patients whose blood contained viral-neutralizing antibodies in comparison with patients not having such antibodies. In addition, it has been reported that the neutralizing antibodies in the blood of AIDS patients bind to gp120 (L. A. Lasky et al., Science, 233:209, 1986; and T. J. Matthew et al., Proc. Natl. Acad. Sci. U.S.A., 83: 9709, 1986).

In one study (Robert-Guroff et al, Nature, 316:72–74, 1985) higher neutralizing titers were observed in the early, asymptomatic and ARC patients than in AIDS patients. The target for neutralization was gp120 and neutralization was strain specific (Matthews et al, Proc. Natl. Acad. Sci. U.S.A., 83:9709–9713, 1986). Immunization of animals with gp120 induced the production of neutralizing antibodies which were all strain specific (Matthews et al, Proc. Natl. Acad. Sci. U.S.A., 83:9709–9713, 1986; Lasky et al, Science, 233:209–212, 1986; Matthews et al, Haematology and Blood Transfusions, 31:414–422, 1987 and Looney et al, Science, 241:357–358, 1988). Subsequently, the immunodominant V3-loop of gp120 was identified as the principal neutralizing domain (amino acids 303–338 of gp120), and strain specificity was associated with hypervariability of this region (Javaherian et al, Proc. Natl. Acad. Sci. U.S.A., 86:6768–6772, 1989). However, antibody to the GPGRAF sequence of the V3-loop will neutralize divergent laboratory strains (Javaherian et al, Science, 250:1590–1593, 1990). In addition to neutralizing antibody to the linear V3-loop, antibodies to the conserved confirmational epitope of gp120 which block gp120-CD4 binding were found to neutralize divergent HIV isolates (Steimer et al, Science, 254:105–108, 1991). Subsequently, several human monoclonal antibodies have been developed (Posner et al, J. Immunology, 146:4325–4332, 1991 and Tilley et al, Res. Virol. 142:247–259, 1991). In addition to epitopes of gp120, other HIV antigens apparently induce broadly neutralizing antibody. These include p17 and gp41 (Robert-Guroff et al, Nature, 316:72–74, 1985 and Dalgleish et al, Virology, 165:209–215, 1988).

Antibody dependent cellular cytotoxicity (ADCC) is an important mechanism of anti-HIV host defense. ADCC mediating antibody is directed at both gp120 and gp41 (Ojo-Amaize et al, J. Immunology, 139:2458–2463, 1987 and Evans et al, AIDS 3:273–276, 1989) and can be present in a serum titer of up to 1:10,000 (Ojo-Amaize et al, J. Immunology, 139:2458–2463, 1987). ADCC titers are higher in early HIV infection than in full-blown AIDS suggesting a relationship to prognosis.

Even more important are reports of passive immunotherapy with high titer anti p24 plasma in patients with HIV infection. This has cleared antigenemia and improved clinical prognosis. (A. Karpas et al., Proc. Natl. Sci. U.S.A., 85:9234, 1988; and G. G. Jackson., Lancet, 2:647, 1988).

Several factors suggest the need for passive serotherapy with monoclonal antibodies. Both prophylactic and therapeutic vaccines have many potential problems. These include genetic variability in HIV, inability to maintain high serum antibody titers after immunization, the presence of several enhancing epitopes on HIV and the poor immune responsiveness of HIV patients. Passive serotherapy has been proposed for both prevention and therapy of HIV infection and effective therapy has been reported in man (Jackson et al. Lancet, 2:647–652, 1988 and Karpas et al. Proc. Natl. Acad. Sci. U.S.A. 85:9234–9237, 1988). In monkeys, serotherapy with serum from animals immunized with whole virus vaccine prevented infection with both HIV-2 and SIVsm (Putkonen et al. Nature, 352:436–438, 1991).

In light of the above background information regarding HIV and AIDS, it is obvious that neutralizing antibodies specific for viral antigens exposed on the surface of the virus or infected cells have great significance in the prevention and/or treatment of this infection.

A number of research groups have already reported successful development of mouse MCA specific for gp120. For example, T. C. Chanh et al. (Eur. J. Immunol., 16:1465, 1986) reported that they chemically synthesized a portion of the peptide chain of gp120 and then prepared an MCA specific for that synthetic peptide. They employed that MCA in the indirect fluorescent antibody technique and reported that they were able to detect HIV infection with greater sensitivity than was possible with the reverse transcriptase determination technique. In addition, Gosting et al. (J. Clin. Microbiol., 25:845, 1987) reported that they solubilized HIV viral antigens, adsorbed them to a column of lentil lectin-Sepharose 4B, collected the glycoprotein fraction thereof and used it to immunize mice, and succeeded in producing anti-gp120 mouse MCA and anti-gp41 mouse MCA. Matsushita et al. (Medical Immunol., 14:307, 1987) also reported achieving viral neutralization with an anti-gp120 mouse MCA. These MCAs are useful in the diagnosis of HIV infection, but they are unfortunately unsuited for the tasks of prevention of HIV infection and treatment of established disease (ARC and AIDS). The reason for this is that, since those MCAs are mouse proteins, they are recognized as foreign by the human immune system if they are administered to the human body. As a result, not only would the MCA activity be inhibited by the anti-mouse MCA antibodies that would be produced by the human immune system, but anaphylactic side effects would also occur. Therefore, it is clear that, for the prevention and treatment of HIV infection in man, it is necessary to develop a human-origin MCA, not a mouse-origin MCA.

In general, human-origin anti-HIV MCAs can be produced by (1) hybridomas obtained by fusion of human B lymphocytes having the ability to produce antibodies specific for HIV and cells of established lymphoid cell lines such as myeloma cells, and (2) lymphoblastoid cells obtained by Epstein-Barr (EB) virus-induced transformation of human B lymphocytes having the ability to produce antibodies specific for HIV. From about 1980 up to the present time, much research has been carried out on the production of human MCAS, but none of those efforts have led to an established method such as in the case of mouse MCAs because each of the approaches described above has its own special problems.

In 1987, there were two reports concerning human MCAs specific for HIV. One was by L. Evans et al. (Proceedings of the Third Congress on AIDS, TP130, 1987). They reported that they employed EB virus to transform lymphocytes from HIV-infected patients and obtained a human MCA which reacted with gag proteins having molecular weights of 55, 41 and 25 kilodaltons. The human MCA belonged to the IgG4 subclass, and it did not neutralize HIV. The second report was by B. Banapour et al. (ibid. TP114). They also employed EB virus to transform lymphocytes from anti-HIV antibody-positive subjects, fused the transformed cells with heteromyeloma cells, and obtained a human MCA which reacted with gp41. This MCA was IgG, but the subclass was not reported. This MCA also did not show HIV-neutralizing activity. Thus, in both of those reports transformation by EB virus was employed. This technique, because it is very efficient at achieving immortalization of human B lymphocytes, is far superior to the cell fusion method. Nevertheless, the obtained lymphoblastoid cell lines produce EB virus or even if they do not produce the virus particles, they contain the EB viral DNA which carries the potential for production of the virus. EB virus has the ability to transform lymphocytes, which means that this virus has tumorigenicity. Therefore, there is worry concerning the safety of using this EB virus transformation technique to produce a drug product for administration to humans.

It is also known that lymphoblastoid cells resulting from transformation of lymphocytes by EB virus can be further infected by HIV, and there is thus the fear that a cell line producing human MCA might be infected by both EB virus and HIV. In addition, the antibody production by lymphoblastoid cell lines presents some disadvantages in view of the facts that it is usually lower and also less stable than the level of production by hybridomas. The reason that Banapour at al. performed additional cell fusion of lymphoblastoid cell lines was to attempt to improve the antibody producing ability of those cell lines.

Accordingly, as seen above, if the immortalization of human B lymphocytes could be achieved with greater efficiency by cell fusion and if a hybridoma having the ability to produce human MCA specific for HIV could be obtained, then the resultant hybridoma would be very desirable on the basis of its having high productivity of an MCA which would moreover be safe for use as a drug.

Recently, additional human and mouse monoclonal antibodies against HIV have been developed (Posner et al. J. Immunology, 146:4325–4332, 1991; Petersen et al. Seventh International Conference on AIDS, WB:2291, 1991; Zolla-Pazner et al. Sixth International Conference on AIDS, 1:152, 1990; Matsushita et al. J. Virol., 62:2107–2114; 1988; and Ho et al. J. Virol. 65:489–493, 1991). Studies have shown that neutralizing antibody directed against the gp120-CD4 binding region are type-specific (Matsushita et al. J. Virol. 62:2107–2114, 1988; Nara et al. J. Virol., 62:2622–2628, 1988; Goudsmit et al. Proc. Natl. Acad. Sci. U.S.A., 85:4478–4482, 1988 and Palker et al. Proc. Natl. Acad. Sci. U.S.A., 85:1932–1936, 1988). The V3-loop formed by a disulfide bond between two cysteine residues at amino acid positions 308 and 338 of gp120 is hypervariable and over 245 gp120 V3-loop sequences from HIV infected individuals have been identified (LaRosa et al. Science, 249:932–935, 1990). Therefore, it is not surprising that this immunodominant region elicits only type-specific neutralizing antibody.

With regard to the subclass which would be the most desirable for human MCAs, it is evident that it would be advantageous for the antibody to be of a subclass which possesses the ability to activate complement and the ability to bind to the Fc receptors on macrophages and lymphocytes. It has been demonstrated that activation of complement by the classical pathway can be achieved by the IgG1 and IgG3 subclasses, whereas IgG2 and IgG4 cannot carry out this activation (J. L. Winkelhake, Immunochem; 15:695, 1978). Furthermore, it has also been shown that the IgG1 and IgG3 subclasses have a strong affinity for the Fc receptors of monocytes (Cosio et al., Immuno., 44:773, 1981). Therefore, for the objective of prevention of infection of cells, it is clear that the IgG1 and IgG3 subclasses are desirable.

However, another consideration is necessary, i.e. that of purification of the produced human MCA. Affinity chromatography using protein A can be effective for the purification of MCAs; and since IgG1 binds to protein A whereas IgG3 does not, it is clear that the IgG1 subclass of human MCA would be the most desirable subclass from the viewpoint of ease of purification.

SUMMARY OF THE INVENTION

The inventors of the present invention, as a result of carrying out vigorous research aimed at obtaining an anti-HIV human MCA and employing a method involving fusion of mouse myeloma cells and lymphocytes from the lymph nodes or spleen of HIV-seropositive donors, succeeded in obtaining a hybridoma which produces a human MCA (IgG1 subclass) specific for gp120, and a hybridoma which produces a human MCA (IgG1 subclass) reacting with both gp120 and gp41. They also succeeded in culturing those hybridomas and/or cell lines originating from those hybridomas and were able to collect the anti-HIV human MCAs from the supernatants of those cell cultures.

That is, the present invention consists of human monoclonal antibodies which are specific for HIV and belong to the IgG1 subclass, specifically an IgG1 antibody which binds with gp120 of HIV, and an IgG1 antibody which binds with both gp120 and gp41 of HIV. In addition, this invention consists of the hybridomas which produce those human monoclonal antibodies and were formed by fusion between human lymphocytes and mouse myeloma cells. These hybridomas have been deposited with the American Type Culture Collection (ATCC) as accession numbers HB9669, HB9670 and HB10074 (S1-1). In addition, another aspect of this invention is the method by which the inventors succeeded in efficiently forming those hybridomas, a method in which human lymphocytes were first treated with complement and anti-human T-lymphocyte mouse MCA or AET treated SRBC and Ficoll and then the treated human lymphocytes were fused with mouse myeloma cells.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1A shows results using AIDS patient serum. FIG. 1B shows results using a healthy donor's serum. FIG. 1C shows results using No. 86. FIG. 1D shows results using subclone 1. FIG. 1E shows results using subclone 2. FIG. 1F shows results using subclone 3. FIG. 1G shows results using subclone 4. FIG. 1H shows results using No. 1. FIG. 1I shows results using S1-1.

FIG. 3 illustrates the results of indirect fluorescent antibody assays to determine the ability of MCA S1-1 to bind to the surface of HIV-infected cells

FIG. 8 shows neutralization of divergent HIV isolates by S1-1 antibody.

FIG. 9 shows the flow cytometry results with HIV-infected ( . . . ) and non-infected cells (_). FIG. 9A: HIV-positive sera. FIG. 9B: S1-1. FIG. 9C: anti-VZV human monoclonal antibody.

Figure 1:
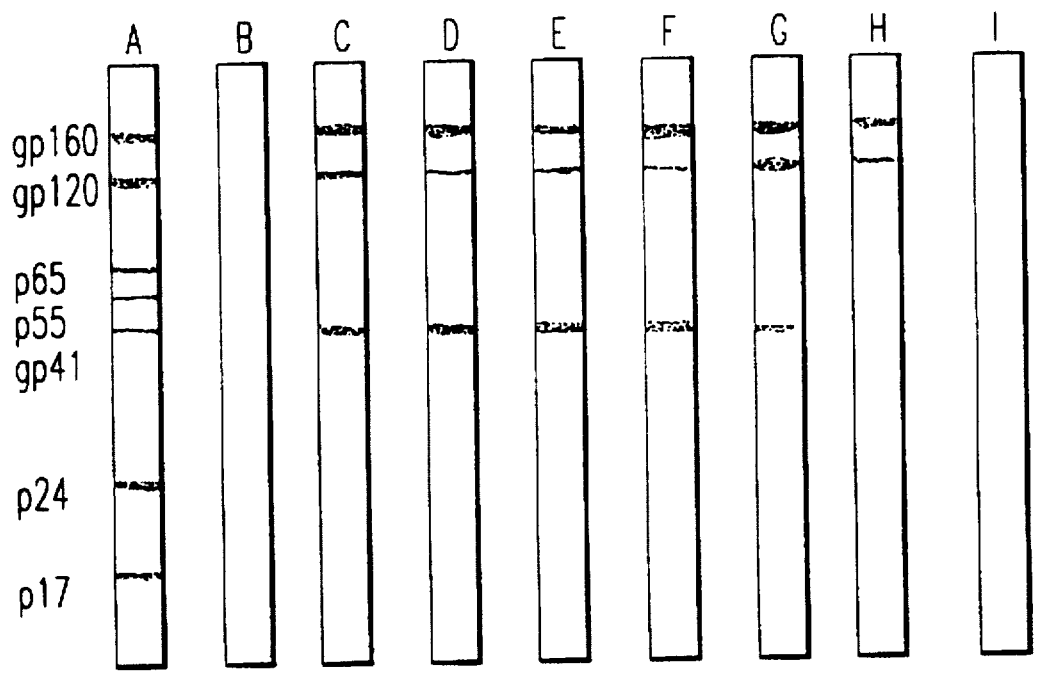
FIG. 1 illustrates the results of a Western blot analysis to determine the viral antigens recognized by the MCAs

Best Mode of Carrying Out the Invention

The human lymphocytes employed in the method of this invention can be obtained from the spleen, lymph nodes, peripheral blood, bone marrow, tonsils, adenoids, etc., of seropositive donors. To achieve the objective of this invention, use can be made of lymphocytes from any of those sources, but it is most desirable that they be obtained from the lymph nodes, spleen or tonsils of seropositive donors or patients with lymphadenopathy.

Preferred human monoclonal antibodies of the present invention are antibodies which block binding of viral gp120 to its CD4 receptor on the lymphocyte surface. Most preferred are antibodies which block gp120-CD4 binding at an ID50 concentration of 100 ng/ml or less obtained from patients having high gp120-CD4 inhibitory titers. One aspect of the present invention is a novel screening method which allows one to identify seropositive donors or patients having lymphocytes which produce antibodies which strongly block gp120-CD4 binding, one measure of virus neutralization. B-lymphocytes obtained from patients identified by the present screening method as producing high-titer antibodies which strongly block gp120-CD4 binding are particularly preferred for use in forming hybridomas.

In the present screening method, multiple well microtiter plates are coated with soluble CD4 (sCD4). Soluble CD4 is commercially available. The sCD4 coated plate is then blocked with non-specific binding protein. Suitable proteins include, but are not limited to, gelatin and albumin, for example. Other non-specific blocking proteins are well known in the art and may be used as the blocking protein in the present screening method. The non-specific blocking protein is generally applied in a buffer, such as phosphate buffered saline, Tween, etc. and incubated at about 37° C. for a sufficient time to block the non-specific binding sites on the CD4 coated wells. Blocking is generally accomplished by incubating the microtiter plate coated with a dilute solution of gelatin in buffer (0.01–1 wt. %) for about 15 minutes–2 hours at 37° C.

Ten-fold serial dilutions of sera obtained from seropositive patients are then prepared and preincubated with recombinant gp120 (0.01–1.0 µg/ml) for a sufficient time to allow immunological binding of the antibodies present in the patient's sera to the gp120. Preincubation may be conducted at room temperature or slightly elevated temperatures (25°–37° C.) for about 15 minutes to about 2 hours in a microtiter plate separate from the microtiter plate coated with sCD4. Recombinant gp120 is commercially available.

After preincubation, the sera/gp120 solution is then added to the sCD4 coated plate and incubated for about 15 minutes–2 hours at room temperature or a slightly elevated temperature (25°–37° C.). The plate is then washed free of excess reagents with buffer. Labeled pooled human anti-HIV antibody is then added to the plate and incubated as before. Detection of the labeled antibody provides a quantitative analysis of the ability of the patent's serum to block gp120-CD4 binding. This is a measure of the antibody titer in the patient's serum which blocks the binding site for CD4 on gp120.

The pooled human anti-HIV antibody may be labeled with any known label which can be directly or indirectly observed or measured. Suitable directly observable labels include radiolabels, biotin pigments, dyes, or other chromogens, spin labels and fluorescent labels. These antibody labels are well known in the art.

Amplification and greater distinction from background can be achieved by the use of enzyme labels or enzyme labelling systems. The substrate is selected to yield the preferred measurable product. Chromogenic and fluorogenic enzymes are preferred. These enzymes and substrates yielding chromogenic and fluorogenic compounds, respectively, are known.

A preferred enzyme is alkaline phosphatase. Use of p-nitrophenyl phosphate substrate produces the p-nitrophenol chromogen. A particularly preferred enzyme is horseradish peroxidase (HRP) which is used with the substrate tetramethylbenzidine (TMB). The optical density (O.D.) at 405 nm can be read on a conventional ELISA reader to quantitate the gp120-CD4 binding activity in patient sera. Generally, aqueous solutions of the enzyme substrate (TMB) containing from $10^{-2}$ and $10^{-10}$ molar, preferably from $10^{-4}$ to $10^{-5}$ molar concentrations of the substrate may be used to develop the chromogen or fluorogen.

After the sera-gp120 solution is added to the sCD4 coated plate and incubated, the plate is washed free of excess reagents and biotinylated pooled human anti-HIV is added to the plate and incubated. The plate is then washed and streptavidin-HRP is added and further incubated. After washing with buffer, TMB is added and the optical density at 405 nm is read using an ELISA reader. Low optical density values correlate with high blocking of gp120-CD4 binding. Patients whose sera exhibit the greatest blocking of gp120-CD4 binding, i.e., gp120-CD4 inhibition titers of greater than 10,000 fold are preferred as a source of B-lymphocytes for subsequent fusion with mouse myeloma cells. The screening method of the present invention is unique because it allows direct identification of both sera and monoclonal antibodies that inhibit the very specific interaction of gp120-CD4 binding.

As the mouse myeloma cells, it is advantageous to employ a cell line which is resistant to 8-azaguanine; and the following are some of the publicly-known cell lines from BALB/C mice: P3x65Ag8, P3-NS1/1-Ag4-1, P3x63AgU1, SP2/OAg14, P3x63Ag8.6.5.3, MPC11-45.6.TG1.7 and SP-1.

In the method of this invention, prior to the fusion of the human lymphocytes and the mouse myeloma cells, it is desirable to treat the human lymphocytes with complement and an anti-human T-lymphocyte mouse MCA (e.g., OKT3, a product of Ortho Diagnostics Co., Ltd.) or to treat the human lymphocytes with AET (Aminoethylisothiouranium Bromide Hydrobromide) treated SRBC (sheep red blood cells) and Ficoll so as to eliminate the human T-lymphocytes. In the actual performance of the method of this invention, for example, a fixed lymphatic tissue is surgically excised from a seropositive human donor and gently dissected with scissors and a scalpel to obtain a liquid containing suspended cells. Then, to remove T-cells from these suspended cells, the following two methods were used:

(1) This suspension is then layered onto a Ficoll-Paque solution, and the lymphocytes are separated and harvested by centrifugation. Then, the lymphocytes are treated with one volume of fresh serum as the source of complement and two volumes of an anti-human T-lymphocyte mouse MCA to destroy the T-lymphocytes and resultant B-lymphocytes are harvested by centrifugation.

(2) This suspension is mixed with AET treated SRBC and then layered onto a Ficoll-Paque solution and B-lymphocytes are separated and harvested by centrifugation. If B-lymphocytes were used instead of nontreated lymphocytes, the hybridoma formation is increased.

The thus-obtained human B-lymphocytes are then fused with mouse myeloma cells. The general conditions for cell fusion and culture of hybridomas are already known, but the inventors nevertheless carried out vigorous research to determine the most desirable combinations for achieving formation of hybridomas and propagation of them and as a result were able to achieve formation of one hybridoma for every $10^4$ lymphocytes treated by the method of the invention.

Those conditions were determined to be as follows. For example, lymphocytes and mouse myeloma cells are mixed at a ratio of 10:1 to 1:100, preferably 1:1 to 1:10, a suitable solution for cell fusion, such as RPMI 1640 containing about 35% polyethyleneglycol (molecular weight: about 1,000–6,000) and about 7.5% dimethylsulfoxide is added, this cell suspension is stirred for one to several minutes at a temperature in the ambient to 37° C. range, this suspension is gradually diluted and then washed with RPMI 1640 containing 10% fetal calf serum (FCS), and finally it is adjusted with HAT (hypoxanthine-aminopterin-thymidine) selective culture solution to give a cell density of $5\times10^5$/ml. Mouse peritoneal exudate cells are added to a 96-well plate as a feeder layer, and the culture solution is removed immediately, before the fused cells are introduced, by dispensing 0.2 ml aliquots of the suspension into the wells of the plate. These are then cultured for 2–3 weeks at 35°–38° C. in humidified air containing 5% $CO_2$. Only hybridoma cells are present in the HAT culture solution, since the 8-azaguanine resistant myeloma cells and cells arising from fusion of myeloma cells cannot survive in the HAT solution (unfused antibody-producing cells die within a few days).

After culturing of the hybridomas in the 96-well plates, the antibody titer of the culture fluid of each well containing cells is determined by the enzyme-linked immunosorbant assay (ELISA) technique, and only hybridomas which produce the desired antibodies are selected. Cells of each selected hybridoma are collected, cloning is performed by the limiting dilution method, and subclones which stably produce an MCA are established. Then those hybridomas are further investigated by analyzing the antigens recognized by their produced MCAs by the Western blot analysis and/or radioimmunoprecipitation analysis technique, and investigating the ability of the produced MCAs to immunologically bind to the surface of HIV-infected cells, and those hybridomas which are producing an MCA which binds to gp120 and gp160 and which is able to bind to the surface of infected cells are finally selected.

The mouse-human hybridomas which were obtained by the method of this invention as described above and which produce anti-HIV human MCAs can be preserved by freezing. If these hybridoma cell lines and/or cell lines derived from them are cultured on a large scale by an appropriate method, it is possible to obtain from the culture supernatant the human MCAs which are the objective of the present invention. In addition, if these hybridomas are transplanted into animals to form tumors, the produced human MCA can be obtained from the ascites or the serum of the animals.

The anti-HTV human MCAs which have been obtained by the methods described above have been found to have the following characteristics.

(1) In ELISA using fixed viral antigens obtained from HIV-infected cells, the MCAs were positive for binding, but they were negative for binding in ELISA using a plastic coated with substances obtained from uninfected cells by the same technique.

(2) Since HIV is composed of many antigenic substances, the Western blot analysis technique and/or RIPA technique was applied to determine the nature of the structural components to which the human MCAs obtained in this invention bind. It was thus found that one of the human MCAs binds to a molecules having a molecular weights of 120 kD and 160 kD (160 kD is the precursor of 120 kD and 41 kD molecules). The second MCA was found to bind to molecules having molecular weights of 41 kD, 120 kD and 160 kD.

(3) The MCAs were investigated to determine whether or not they bind to the surface of HIV-infected cells. After the human MCA was reacted with unfixed HIV-infected cells, fluorescein-labeled antibody to human IgG was allowed to react, and strong fluorescence was observed on the surface of the infected cells. Therefore, it was learned that all of the human MCAs of this invention bind to the surface of infected cells.

(4) Human IgG is known to have four subclasses, i.e., IgG1, IgG2, IgG3 and IgG4, with each subclass having its own characteristic biological activities. Each of the anti-HIV human MCAs obtained in this invention was thus investigated for its subclass using a specific animal antiserum, and it was found that all of the MCAs of this invention belong to the IgG1 subclass.

EXAMPLES

Experimental Example 1

A. Cell Fusion

1. Collection of Lymphocytes

A lymph node which was surgically excised from an ARC patient was finely minced using scissors and a scalpel. Cells therefrom were suspended in medium A (RPMI 1640 containing 10% fetal calf serum (FCS), 2 mM glutamine, 1 mM sodium pyruvate, 20 µg/ml L-serine, 0.05 µ/ml human insulin and 80 µg/ml gentamicin sulfate). This cell suspension was layered onto a Ficoll-Paque solution and centrifuged at 1,500 rpm for 20 min. The cells which collected on the top of the Ficoll-Paque solution were harvested, centrifugally washed once with phosphate-buffered saline (PBS) and twice with RPMI 1640. Finally, the cells were resuspended in RPMI 1640 to a concentration of $1 \times 10^7$ cells/ml.

2. Treatment of Lymphocytes

To reduce the amount of cell fusion that would take place with T-lymphocytes, the T-lymphocytes in the lymphocyte suspension were eliminated by either of the following two methods.

(1) OKT3 (Ortho Diagnostics Co., Ltd.) was added to the above-mentioned cell suspension to give a final 200-fold dilution. After reacting at 4° C. for 60 minutes, the cells were precipitated by centrifugation (1,500 rpm for 5 min). Next, baby rabbit complement was diluted 3-fold (with RPMI 1640) and added to the cell pellet to obtain a suspension, which was then reacted at 37° C. for 60 min. This cell suspension was then twice subjected to centrifugal washing.

(2) The same volume of $1 \times 10^8$ AET treated SRBC suspension in medium A was added to the above-mentioned cell suspension. After gently mixing at room temperature for 5 minutes. The cells were precipitated by centrifugation at 1000 rpm for 5 minutes. The cell pellet was incubated at room temperature for 20 minutes, then gently suspended, and layered onto Ficoll-Hypaque. After centrifugation at 1500 rpm for 20 minutes, the B-lymphocyte fraction was collected from the interface layer of the medium and the Ficoll-Hypaque and subjected to centrifugal washing.

3. Cell Fusion

The OKT3-treated or AET rosette treated lymphocytes or untreated lymphocytes were each mixed with mouse myeloma P3U1 cells (both cell populations were $3 \times 10^7$ cells) in RPMI 1640 medium. These cell mixtures were then precipitated by centrifugation (1,600 rpm, 5 min). The supernatant was discarded, and the cell pellet was broken up by tapping the tube. Then 1 ml of polyethylene glycol solution (35% v/v polyethylene glycol No. 1000 and 7.5% v/v dimethylsulfoxide in RPMI 1640) was slowly added to the tube, and this was allowed to stand for one minute at room temperature. Next, 2 ml of RPMI 1640 was added, and was allowed to stand for one minute; another 2 ml of RPMI 1640 was added, and was allowed to stand for 2 minutes. Then 4 ml of HAT medium (95 µM hypoxanthine, 0.4 µM aminopterin, and 16 µM thymidine in medium A) was added, and the mixture was allowed to stand for 2 minutes; another 8 ml of HAT medium was added and the mixture was allowed to stand for 2 minutes; an additional 24 ml of HAT medium was added and the mixture was allowed to stand at 37° C. for 30 minutes. Finally, the total volume was made up to between 75 and 150 ml by the addition of HAT medium.

Aliquots of approximately 200 µl were seeded into the wells of a 96-well flat culture plate. This culture plate had been pretreated by seeding ICR mouse (male) peritoneal exudate cells at $2 \times 10^4$ cells/well; immediately prior to the seeding of the fused cells, the culture fluid was removed from the wells. This culture plate was then incubated at 37° C. in a $CO_2$ incubator. Once per week, half of the culture medium in each well was replaced by HT medium (HAT medium from which aminopterin had been left out), and the incubation was continued until hybridoma colonies became apparent.

4. Cloning

At the time when hybridoma colonies became apparent, each of the culture fluids was treated for the presence of antibody activity directed at HIV. The hybridomas of colonies which were found to be producing HIV-specific antibodies were then cloned. First, 96-well flat plates were seeded with only mouse peritoneal exudate cells at 2×10⁴ cells/well. Then, at various times from one hour to one day after the seeding, the culture medium was removed and the hybridomas were seeded into 96 wells each at 10 cells/well. For the first cloning, HT medium was employed, while medium A was used for the second cloning. After 2-3 weeks of culture, the antibody activity was determined, and positive clones were picked up. B. ELISA (Enzyme-Linked Immunosorbent Assay)

1. Viral Antigens a. HTLV-III (human lymphotropic virus type III) antigen (Bionetics Laboratory Products Co., Ltd.)

b. CR10/NIT Antigens

CR10/NIT is a cell line which was established by creating a persistent infection of CEM cells with the NIT strain of HIV. The viral antigens were partially purified from this CR10 cell line. In brief, CR10/NIT cells were washed 3 times with PBS and then frozen at −70° C. At the time of use, the frozen cells were thawed, and 10⁸ cells were suspended in 9 ml of distilled water; this cell suspension was vigorously agitated for one minute using a Vortex blender. This was then centrifuged for 10 minutes at 2,800 rpm, and the supernatant was collected. One ml of 10-fold concentrated PBS was next added to the supernatant, centrifugation was performed at 15,000 ×g for 30 min, and the pellet was collected. The pellet was resuspended in 5 ml of PBS containing 0–1% Triton X-100 and 1 mM PMSF, sonicated 4 times for 15 sec each while chilling in ice and allowed to stand for a further 30 minutes while chilling in ice; the supernatant was then collected. The supernatant was subjected to ultracentrifugation at 100,000 ×g for one hour, and the supernatant was employed as the viral antigen preparation. As the negative control, an antigen preparation was obtained by treating CEM cells (uninfected by HIV) in the same manner.

2. Antigen-Coated Plates

HTLV-III antigen (1 µg/ml), CR10/NIT antigens (20–25 µg/ml) and CEM antigens (20–25 µg/ml) were each dispensed in aliquots of 50 µl wells of separate microtiter plates (Coster, No. 3912), and the plates were then allowed to stand at 37° C. for 60 min. The plates were then washed twice with HBSS-BSA (Hank's balanced salt solution, 0.5% bovine serum albumin and 0.1% NaN₃), PBS (Ca⁺⁺, Mg⁺⁺) containing 3% BSA was dispensed at 125 µl/well, and the plates were allowed to stand at 37° C. for 60 min and then at 4° C. overnight to carry out blocking.

3. ELISA

The antigen-coated plates were washed twice with HBSS-BSA, and then 50 µl of each of the heated (56° C. for 60 minutes) hybridoma culture fluids was added. After letting these react at room temperature for 60 minutes, the plates were again washed twice with HBSS-BSA. Then 50 µl of alkaline phosphatase-conjugated goat antibody to human IgG (diluted 1000 ×; Tago Inc.) were added, and reaction was again allowed to take place at room temperature for 60 minutes before the plates were washed 4 times with HBSS-BSA. Next, 100 µl of 0.05M carbonate buffer containing 1 mg/ml p-nitrophenylphosphate and 1 mM MgCl₂, pH 9.5, was added to each well, and the plates were reacted at room temperature for 60 minutes or overnight. Finally, the optical density was measured at 405 nm using an ELISA Reader (Titertech Inc.).

C. Experimental Results

1. Lymph node cells from Patient A were compared with and without OKT3 treatment.

TABLE 1

Generation of Hybridomas Producing IgG Antibodies to HIV*

| Treatment | Number of Anti-HIV IgG-Positive Wells | | |
|---|---|---|---|
| | High O.D.** | Medium O.D. | Low O.D. |
| −OKT3 | 3 | 2 | 1 |
| +OKT3 | 6 | 5 | 6 |

*Indicates wells containing hybridomas which produce IgG that reacts with CR10/N1T antigens but not with negative control (CEM antigens).
**"High" means that the optical density at 405 nm was larger than 1.0, while "Medium" indicates the 0.4–1.0 range and "Low" represents the 0.2–0.3 range. Therefore, more hybridomas producing IgG antibodies to HIV were generated in the case of the lymphocytes which were treated with complement and anti-lymphocyte antibody.

2. As reported above, hybridomas were obtained by fusion of mouse myeloma cells with OKT3-treated lymphocytes from the lymph nodes of patients with ARC, those hybridomas were cloned, and the inventors successfully established hybridomas No. 86 (ATCC No. HB9669) and No. 1 (ATTC No. HB9670), which stably produce MCAs. On the other hand, hybridoma S1-1 (ATCC No. HB-10074) which stably produces MCA was obtained by fusion of mouse myeloma cells with AET rosette treated lymphocytes from the spleen of patients with ARC. In ELISA, the MCAs produced by hybridomas No. 86, No. 1, and S1-1 reacted with HTLV-III antigen and CR10/NIT antigens but not with CEM antigens. The MCA production rates were 10 µg/10⁶ cells/day in the case of No. 86, 20 µg/10⁶ cells/days in the case of No. 1, and 5 µg/10⁶ cells/day in the case of S1-1.

Experimental Example 2

A. Purification of MCAs

The culture fluids (1.5–2 liters) of hybridomas No. 86, No. 1, and S1-1 were used as the starting materials. Ammonium sulfate was added to the culture fluids to 50% saturation, and the resultant protein precipitates were collected by centrifugation at 10,000 rpm for 30 min. The precipitates were then dissolved in a suitable volume of PBS, followed by dialysis against PBS. The dialyzed solution was next applied to a protein A-Sepharose column bed (bed volume: 6 ml; Pharmacia AB). The column was washed with saline, and then the IgG was eluted with HCl in saline (pH 2.5). The IgG eluted in this manner was confirmed to be pure by sodium dodecyl sulfate-polyacrylamide gel electrophoresis (SDS-PAGE).

B. Identification of IgG Subclasses of MCAs

1. Heavy Chains

The purified MCA solutions were reacted with sheep antisera to human IgG1, IgG2, IgG3, and IgG4 (Serotec Inc.). The subclass of each MCA was identified on the basis of which antisera resulted in formation of an immunoprecipitation ring. It was thus found that No. 86, No. 1, and S1-1 MCAs reacted only with the anti-IgG1 and did not react with the other three antisera. Therefore, all of these anti-HIV MCAs were identified to be IgG1.

2. Light Chains

A microtiter plate was coated with goat antibody to human IgG (Tago Inc.). Each of the purified MCAs was then reacted with this anti-human IgG-coated plate. Next, in accordance with the method for ELISA described earlier in section B. of Experimental Example 1, alkaline phosphatase-conjugated goat antibodies to human lambda chain and to kappa chain (Tago Inc.) were employed and the type of each MCA was identified. As a result, No. 86 MCA was shown to have a kappa chain, while No. 1 MCA and S1-1 MCA were found to have lambda chains.

C. Viral Antigens Recognized by the MCAs

The Western blot method (Bio Rad Immunoblot Assay; Bio Rad Inc.) was employed to identify which viral antigens were recognized by MCAs No. 86 and No. 1. MCA No. 1 has also been referred to as MCA 1.2 by the inventors; thus, MCA 1 and MCA 1.2 refer to the same cell line. The procedures of the assay technique are briefly described as follows.

The HTLV-III strain of HIV was applied to SDS-PAGE, the separated viral antigens were blotted on nitrocellulose strips, and each of the semi-purified MCAs was reacted thereon. Next, peroxidase-conjugated antibody to human IgG was reacted with the strips, and finally, to develop color, an enzyme substrate was reacted with the strips. The results are shown in FIG. 1. In the Figure, A is serum from an AIDS patient, B is serum from a normal human, C is No. 86, D to G are subclones of No. 86, H is the clone of No. 1, and I is S1-1.

MCA No. 86 reacted strongly with gp41 and reacted weakly with gp120. As the reason for reacting with both gp41 and gp120, it is possible that MCA No. 86 was a mixture of one MCA which-reacted with gp41 and another MCA which reacted with gp120. To investigate this possibility, the hybridoma producing MCA No. 86 was again cloned, yielding subclones 1, 2, 3, and 4, and the MCA produced by each of those subclones was also subjected to the Western blot assay. As seen in D, E, F and G, the MCA from each of the 4 subclones of hybridoma No. 86 reacted with both gp41 and gp120.

This finding suggests that MCA No. 86 either recognizes an antigenic epitope which is present on both gp41 and gp120, or is an antibody directed at the cleavage site of gp41 and gp120. MCA No. 86 also reacted with gp160, and the reason for this is that this antigen is a glycoprotein constructed from gp41 and gp120.

MCA No. 1 reacted with gp120. It, of course, also reacted with gp160, which is the precursor of gp120.

MCA S1-1 did not react with any antigen on Western Blotted paper.

D. Radioimmunoprecipitation assay (RIPA)

It sometimes occurs that some antigenic determinants recognized by MCAs are not detected by the Western blot analysis. This is thought to be due to the destruction of tertiary structure of antigens by strong detergent, heat, and methanol treatment of antigens used in the Western blot assay. This phenomenon was observed in the case of MCA S1-1. Therefore, the antigens recognized by MCA S1-1 was determined by RIPA as follows.

$^{35}$S labeled cell extracts for RIPA were prepared as follows. MOT cells or HTLV III (IIIb, MN, or RF strain) infected MOT cells (4 days after infection the MOT was equal to $10^3$ TCID$_{50}$/5×10$^6$ cells) were labeled with $^{35}$S-cysteine and $^{35}$S-methionine (50 μCi/ml total activity). The labeling media was RPMI 1640 containing 1/10 the normal concentration of methionine, 10% extensively dialyzed fetal calf serum, the other essential amino acids and the $^{35}$S labeled amino acids. Uninfected and infected MOT cells were cultured 14 hours in the labeling media and then washed with PBS(-). The culture supernatants containing virus particles were lysed with RIPA buffer (2 mM Tris-HCl pH 7.4, 1% deoxycholate, 1% Triton X-100, 0.1% sodium dodecylsulfate and 1 mM (p-amidinophenyl) methanesulfonyl fluoride). The lysate was used as labeled antigens. The labeled antigens were divided and treated with 10 mM dithiothreitol (DTT) at 37° C. for 30 minutes or incubated in the absence of DTT for 30 minutes. The labeled antigens were immunoprecipitated by the MCA S1-1 and HIV+ human serum antibodies conjugated to protein-A sepharose beads in the presence of RIPA buffer.

Figure 2:
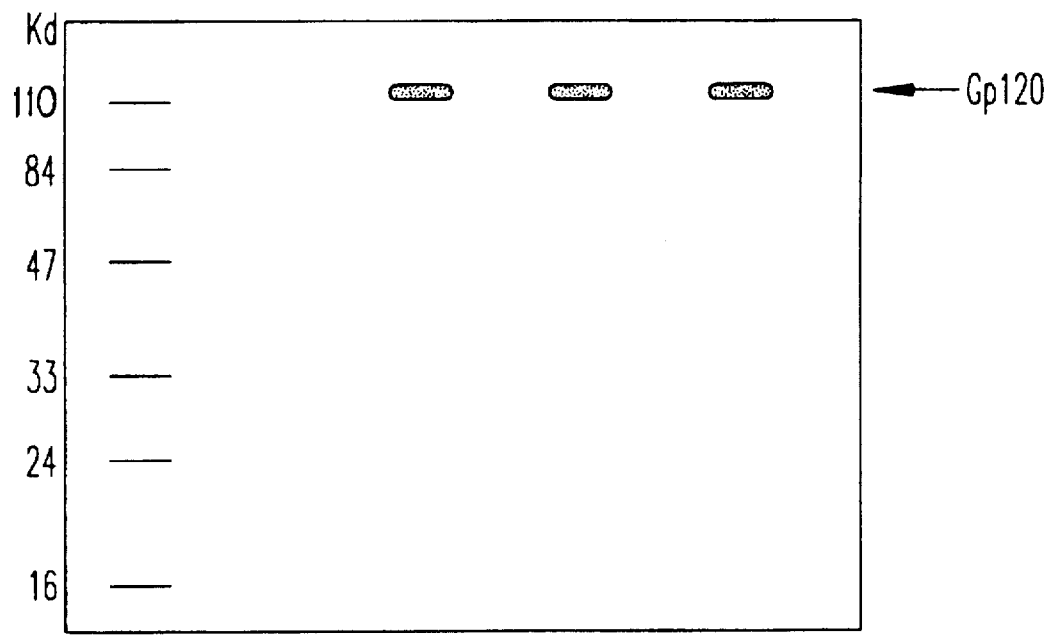
FIGS. 2 illustrates the results of radioimmunoprecipitation assay to determine the antigenic determinants recognized by MCA S1-1.

Labeled antigen-antibody complex conjugated to protein A-sepharose beads were washed eight times with RIPA buffer, twice with 10 mM Tris HCl pH 6.8, and then suspended in sample buffer (62.5 mM Tris HCl pH 6.8, 1% SDS, 20% glycerol, 0.2% bromphenol blue) in the presence of 2% 2-mercaptoethanol. After heating the suspension at 100° C. for 3 minutes, released labeled antigens were separated on a 10% acrylamide gel. After electrophoresis, the gel was fixed with 50% methanol-10% acetic acid, immersed in 1M salicylic acid—3% glycerol, and dried using gel drier. The dried gel was autoradiographed at -80° C. for 3 to 5 days. From FIG. 2, the following results were obtained:

(1) MCA S1-1 recognizes gp120 of three strains of HTLV-III (IIIb, MN and RF).

(2) The antigenic determinant on gp120 (gp160) was easily destroyed by sulfhydryl reagents.

E. Binding to Surface of HIV-Infected Cells

The ability of MCAs No. 86, No. 1, and S1-1 to bind to the surface of HIV-infected cells was investigated by the indirect fluorescent antibody technique.

MOT cells (an HTLV-II transformed cell line), 5×10$^6$ cells, were mixed with 2.5×10$^6$ TCID$_{50}$ of HTLV- IIIb, and this mixture was incubated at 37° C. for 2 hr to permit infection to proceed. These cells were then cultured for 3 days in RPMI 1640 medium containing 10% FCS, after which the cells were washed 3 times at 4° C. with PBS containing 0.1% NaN$_3$. As the negative control, MOT cells which were not infected with HIV were employed.

These unfixed cells were dispensed into conical tubes to give 2×10$^6$ cells/tube, and centrifugation was performed at 1,500 rpm for 5 minutes. The supernatant was discarded, and the cell pellet was suspended in 100 μl of 50 μg/ml MCA in 0.1% NaN$_3$-HBSS. This suspension was reacted at 4° C. for 60 minutes, and then the cells were washed 3 times with 0.1% NaN$_3$-1 mM EDTA-PBS. Each cell pellet was suspended in 100 μl of fluorescein isothiocyanate-labeled antibody to human IgG (50×dilution; Tago Inc.), followed by reaction at 4° C. for 60 minutes.

The cells treated as described above were next analyzed by flow cytometry (FACSkan; Becton Dickinson, Co.). The status of binding was investigated for the following combinations: HTLV-IIIb-infected MOT cells and serum (100× diluted) from an AIDS patient, uninfected MOT cells and serum (100× diluted) from an AIDS patient, HTLV-IIIb-infected MOT cells and MCA S1-1, uninfected MOT cells and MCA S1-1, HTLV-IIIb-infected MOT cells and MCA V1, and uninfected MOT cells and MCA V1. V1 was an IgG human MCA specific for an irrelevant antigen.

Figure 3A:
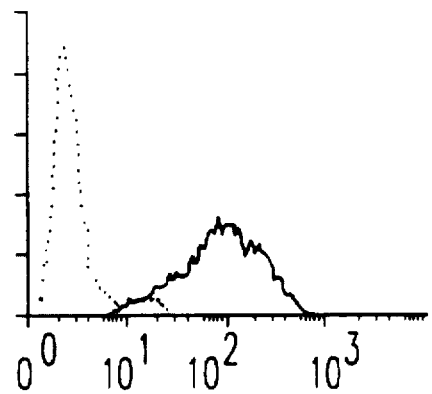
FIG. 3A shows results using patients' serum.
Figure 3B:
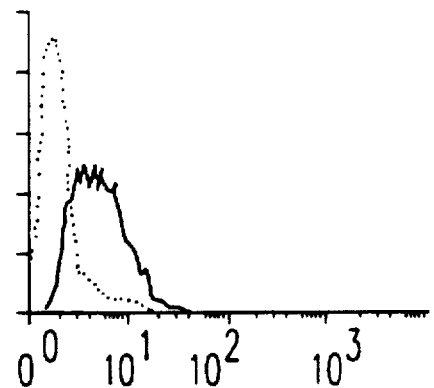
FIG. 3B shows results using antibody S1-1.
Figure 3C:
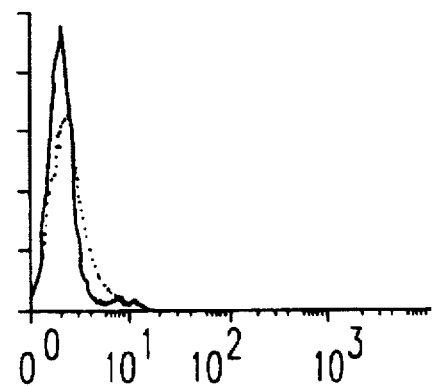
FIG. 3C shows results using V1.

The following results were obtained. MCA S1-1 bound to the surface of HIV-infected cells, but it did not bind to the uninfected cells. The same results were obtained with MCA No. 86 and MCA No. 1. MCA VI, which was not specific for HIV, did not react with the HIV-infected cells (FIG. 3).

With an MCA which reacts with the surface of virus-infected cells, it can be speculated that it might be possible to destroy the infected cells in the presence of complement or in the presence of lymphocytes or macrophages, thereby stopping the production of new virus and permitting suppression of the spread of the infection.

F. Neutralization assay

The neutralizing assay of the MCAs was performed by two methods: neutral red dye uptake and p24 antigen capture. As used herein, the term "neutralization" means preventing the infection of lymphocytes with HIV. The neutral red dye uptake neutralization assay is based on the following premise: when HIV infects permissive cells, the cells lyse after a short time. Neutral red dye is incorporated into the cytoplasm of viable cells. In the neutral red dye uptake neutralization assay, if a MCA could bind to HIV and prevent it from entering permissive cells, the cells would remain viable and they would take up neutral red dye, giving a calorimetric indication of cell survival which would be indicative of the neutralization of HIV. The protocol is given below.

Protocol for Neutralization Assay; Neutral Red Dye Uptake

Supernatant from HTLV-IIIb infected H9 cells was used as a virus source for the neutralization assays. A Multiplicity of Infection (MOI) of 20–25 was mixed with dilutions of anti-HIV antibody and incubated for 1 hour at 37° C. HIV mixed with an irrelevant MCA or HIV mixed with HIV positive serum were used as controls. After the virus-antibody incubation, a CD4+ cell line (MOT) was added at $3 \times 10^4$ cells/well. These plates, containing HIV, antibody, and MOT cells were then incubated for either 5 or 6 days. On day 5 or 6, the cells in the 96-well microtiter plates were suspended by micropipette action and 100 μl was transferred into corresponding wells of a poly-L-lysine coated plate containing 100 μl of 0.014% neutral red dye in media. The neutral red dye containing plates were incubated for 1 hour at 37° C. All the cells attach to the poly-L-lysine on the bottom of the well while only the viable, undamaged cells took up the neutral red dye. After 1 hour, the plate was washed free of excess dye and 100 μl of 1% acetic acid in 70% ethanol was then added to the 96-well plates. The cells containing the dye lysed and released the dye into the supernatant. A calorimetric determination of cell survival was made using a Titertek ELISA reader at 540 mM.

Results: Neutral Red Dye Uptake

Figure 4:
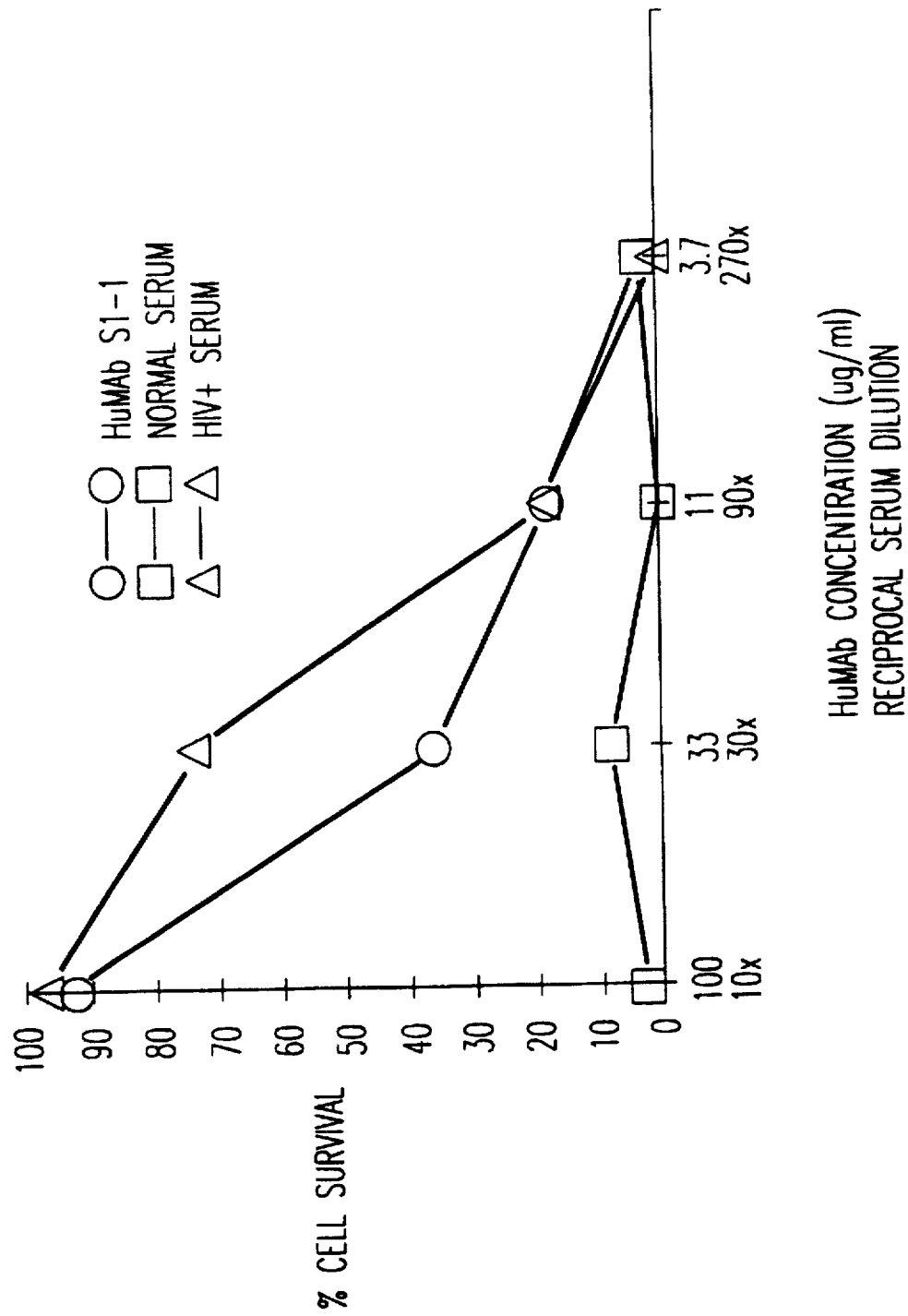
FIG. 4 illustrates the results of a neutral red dye uptake assay to determine the ability of MCA S1-1 to neutralize HIV-IIIb.

The following results were obtained in the neutral red dye uptake neutralization assay. MCA S1-1 was observed to neutralize over 90% of the infectious HIV at a concentration of 100 μg/ml as measured by the neutral red dye uptake, cell survival assay (FIG. 4). As the concentration of MCA S1-1 decreased, it inhibited less HIV from infecting the permissive cell line, MOT. Normal serum did not inhibit HIV infection at all, while HIV-positive serum inhibited HIV infection to a 90-fold dilution. Neither MCA S1-1 nor HIV-positive serum effectively neutralized HIV at concentrations less than 11 μg/ml or at greater than 90-fold dilutions, respectively.

Protocol for Neutralization Assay
Antigen Capture Assay

Another HIV neutralization assay was performed that detects the p24 HIV core protein in an ELISA antigen capture assay. When HIV infects permissive cells, it replicates itself inside the cell and releases viral particles from the cell into the surrounding supernatant where they can be detected. Again, if a MCA were to bind to HIV and inhibit penetration into the cell, HIV could not replicate itself and would not release viral particles into the supernatant. The p24 antigen capture was performed as follows.

Cell-free HTLV-IIIb infected H9 supernatant at a MOI of 20–25 was incubated with dilutions of anti-HIV antibody in 96-well microtiter plates for 1 hour at 37° C. It is important to note that the amount of HIV inoculum could not be detected by this antigen capture assay. Only the viral particles produced by HIV infected cells are detected. HIV mixed with an irrelevant MCA or HIV mixed with HIV-positive sera were used as controls. After the virus-antibody incubation, a CD4+ cell line (MOT) was added to the plates at $3 \times 10^4$ cells/well. These plates containing HIV, antibody, and MOT cells were then incubated for 7 days. Samples of the supernatants were taken from each well at 3, 5, and/or 7 days. These samples were heat-inactivated for 1 hour at 56° C. and then added to 96-well ELISA plates coated with 5 μg/ml of HIV-positive serum. After 1 hour incubation at room temperature, the ELISA plates were washed with 0.05% Tween-20 in phosphate buffered saline. Then a biotinylated MCA specific for p24 (Western Blot) was added to the plates at 2 μg/ml, and the plate was incubated and washed as before. Streptavidin conjugated alkaline phosphatase was then added to the plate at a concentration of 1 μg/ml, incubated for 1 hour and washed free of excess reagent. One mg/ml of para-nitrophenyl phosphate in carbonate buffer pH 9.5 was added to the plate and the optical densities of the wells were read on a Titertek Multiskan ELISA reader at 405 nm. An increase in optical density indicated that more p24 was present in the original culture supernatant.

Results: p24 Antigen Capture

Figure 5:
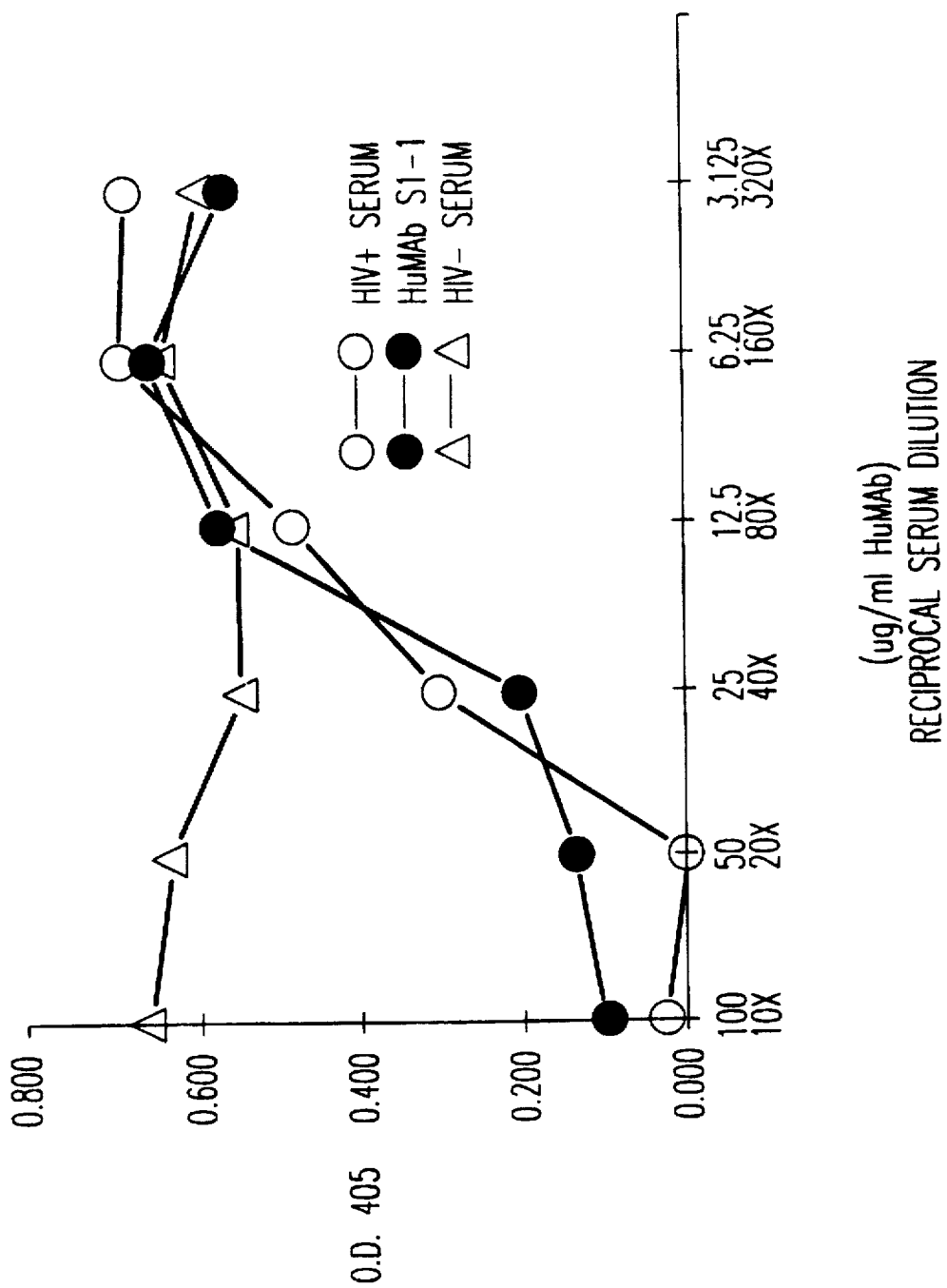
FIG. 5 illustrates the results of an antigen capture assay to determine the ability of MCA S1-1 to neutralize HTLV-IIIb.

The following results were obtained from the HIV p24 antigen capture neutralization assay. MCA S1-1 blocked HIV infection significantly as evidenced by low levels of the p24 HIV core protein in the presence of S1-1 concentrations of from 125 to 100 μg/ml (FIG. 5). S1-1 did not maintain neutralization at lower concentrations. HIV-positive serum completely neutralized infection at 10-fold and 20-fold dilutions and partially neutralized HIV at a 40-fold dilution, but also did not maintain neutralization at higher dilutions as indicated by high levels of p24.

Discussion

MCA S1-1 neutralizes HIV infection in permissible cells. The degree of neutralization depends on the concentration of the MCA. At high concentrations (100 μg/ml) S1-1 inhibits 93% of cell-free HIV from infecting cells in a cell survival assay. Although S1-1 lost the capacity to neutralize HIV at lower concentrations, HIV-positive serum also lost the ability to neutralize at high dilutions. Consistent with the cell survival assay results, less p24 HIV core protein was produced in the presence of S1-1, indicating that S1-1 inhibits HIV infection.

The results of the various experiments described above are compiled in the following Table 2.

TABLE 2

| Property | No. 86 | No. 1 | S1-1 |
|---|---|---|---|
| Isotype of MCA | IgG1.κ | IgG1.λ | IgG1.λ |
| Binding to HIV in ELISA | HTLV-IIIb CR10/N1T | HTLV-IIIb CR10/N1T | HTLV-IIIb CR10/N1T |
| Binding to HTLV-IIIb infected cells | | | |
| fixed | + | + | + |
| unfixed | + | + | + |
| Viral antigens recognized by MCA | gp120, gp41 | gp120 | gp120 |
| Neutralization | − | − | + (90% at 100 μg/ml dye uptake method) |
| MCA production rate (μg/$10^6$ cells/day) | 10 | 20 | 5 |

Neutralizing Specificity of S1-1 Antibody

Methods

Cells and virus

Infectious virus was obtained from cell-free supernatants of H9 cells infected with HIV/IIIB, MN, and RF (provided by Dr. Robert Gallo to the NIAID AIDS research and reference reagent program). Clinical isolate #20 (provided by Dr. Paul Feorino at the Centers for Disease Control in Atlanta, Ga.) was also propagated in H9 cells. Viral stocks were made and frozen at −70° C. for neutralization assays. Both non-infected cells and infected cells were propagated in RPMI 1640 (Flow Labs) containing 10% fetal calf serum and 125 µg/ml gentamicin (Gibco). MoT cells were used as target cells for neutralization assays and antigen preparations. MoT cells are a 95% CD4+ cell line that is permissive, highly cytopathic and 100% lytic when infected with HIV-1 (Saxon et al, Ann. Interm. Med., 88:323–326, 1978).

Fusion

A single cell suspension was made from the spleen of an HIV sero-positive patient who underwent clinically-indicated splenectomy. The suspension was incubated in a flask for 1 hour at 37° C. to remove adherent macrophages and then non-adherent cells were transferred to another flask. The lymphocytes were then depleted of T-cells by a resetting procedure. Sheep red blood cells (sRBC) were treated with AET (2-aminoethyl isothioronium bromide hydrobromide) and added to the lymphocytes such that the ratio of the SRBC pellet volume to the lymphocyte pellet volume was 10 to 1. The sRBC-lymphocyte mixture was then suspended and incubated for 30 minutes. Then a ficoll hypaque separation was performed and the B-cell fraction was removed from the interface (buffy coat). The final preparation of cells contained greater than 90% B-cells as determined by immunofluorescence.

Then $9 \times 10^6$ B-cells were fused with $18 \times 10^6$ of the mouse myeloma cell line P3x63AgU1 (Yelton et al, Lymphocyte Hybridomas, New York Springer-Verlag, 1985) in the presence of 35% polyethylene glycol and 7.5% dimethylsulfoxide in RPMI 1640. The cells were plated in 96-well microtiter flat-bottom plates containing mouse peritoneal macrophages as a feeder layer at a density of $10^4$/well. Hybridomas were selected in RPMI 1640 containing hypoxanthine (95 µM), aminopterin (0.4 µM) and thymidine (16 µM) as selective additives. Approximately 14 days post fusion, supernatant samples were taken from the well containing hybridomas and assayed for anti-HIV human IgG activity.

Screening/Cloning

Hybridomas were screened for anti-HIV human IgG antibody secretion by ELISA methodology. The ELISA was performed by incubating hybridoma supernatants with the infected and non-infected cell lysate-coated ELISA plates for 1 hour. The plates were washed free of hybridoma supernatant and alkaline phosphatase-conjugated goat anti-human IgG (Tago) was added at 14 g/ml and incubated for 1 hour. Then the plates were washed free of the second antibody and 1 mg/ml of p-nitrophenyl phosphate (Sigma) in carbonate buffer (pH9.5) was added and the optical densities of each well were read at 405 nm on a Titertek Multiskan ELISA reader 4 to 12 hours later. The ELISA-positive anti-HIV antibody secreting hybridomas were cloned over 5 times by limiting dilution to ensure monoclonality.

Antibody purification and characterization

Anti-HIV supernatants from mass culture were ammonium sulfate precipitated and then the IgG was purified using a protein A-sepharose column (Pharmacia). The purity of the IgG was confirmed by SDS-PAGE. Single Radial Immunodiffusion (SRID) plates (ICN) were used to determine the isotypes of the antibodies. Anti-human kappa and lambda chain specific second antibodies (Tago) were used in ELISA to determine the light chain subtype. The concentrations of the human monoclonal antibodies (HuMAbs) were determined by SRID. Western blotting (DuPont) was performed according to the manufacturers instructions using the HuMAbs and HIV positive and negative serum as controls.

Flow cytometry

MoT or H9 cells infected with either HIV/IIIB, MN or RF and non-infected cells were incubated at 4° C. for 1 hour with either 100 µl hybridoma supernatants, HIV positive sera, or an irrelevant HuMAb (anti-Varicella Zoster Virus, anti-VZV) and then washed. FITC conjugated goat anti-human IgG (Tago) was added to the cells and incubated as before. The cells were then washed free of excess second antibody, fixed with 1% formalin and their surface immunofluorescence was analyzed on a Becton Dickinson FACS-kan Analyzer.

Radioimmunoprecipitation assay (RIPA)

RIPA was performed using a modification of Allan et al (Science, 228:1091–1093, 1985). Radio-labeled cell extracts were prepared by the addition of a $^{35}$S-cysteine/methionine mixture (ICN) (50 µCi/ml) to both $5 \times 10^6$ non-infected and HIV infected MoT cells. Prior to labeling, cells were grown in 1/10 h methionine RPMI 1640 containing 10% dialyzed fetal calf serum. The cells were incubated in the presence of labeling media for 14 hours. Then the cells were washed once in PBS and lysed in RIPA buffer (20 mM Tris-HCl pH7.4, 1% deoxycholate, 1% Triton X-100, 0.1% SDS and 1 mM PMSF). The lysate was clarified by high speed centrifugation (32,000×g for 1 hour). In some experiments the labeled antigens were enriched for glycoproteins on a lentil lectin-Sepharose column (Pharmacia) according to the instructions provided with the product. The purified HIV glycoproteins were divided into two fractions and one of them was treated with 5 mM DTT to destroy conformational structure of viral proteins. The HIV antigens were incubated with S1-1, HIVIG (provided by Dr. Alfred Prince to the NIAID AIDS Research and Reference Reagent Program), or HIV negative serum. Protein A Sepharose was added to the mixture which bound the antigen-antibody complexes and then was washed free of unbound antigen several times with RIPA buffer. Immunoprecipitated antigen was boiled for 5 minutes and then electrophoresed on a 10% polyacrylaminde gel. After electrophoresis the gel was dried, exposed to Kodak X-Omat film and the autoradiograph was developed 3–4 days later.

Neutralization assay

The neutralization test was performed by incubating 50 µl of 200 tissue culture infectious dose 50 (TCID50) of HIV/IIIB, MN, RF or clinical isolate #20 with 50 µl of serial three-fold dilutions of S1-1, HIVIG, or an anti-gp41 HuMAb, No. 86 in 96-well plates. In complement-dependent neutralization assays, guinea pig complement (Pelfreez) was added to the anti-body-virus mixture at a final dilution of 1:20. After a 1 hour incubation at 37° C., $3 \times 10^4$ MoT cells (100 µl) were added to the HIV-antibody mixture. The plates were then incubated for 7 days at 37° C. in a humidified 5% $CO_2$ chamber. To quantitate neutralization, cell survival in the presence of anti-HIV antibody was measured using a similar procedure to that of Montefiori et al (J. Clin. Microbiol., 26:231–235, 1988). 100 µl of the remaining MoT cells in the neutralization cell culture plate were suspended by micropipette action and added to poly-L-lysine coated plates containing 100 µl of 0.014% neutral red dye (Sigma). The plates were incubated for 1 hour and washed free of excess dye. The 1% acetic acid in 50% methanol was added to the plates to lyse the cells containing dye and the color development was quantitated at 540 nm on a Titertek Multiskan ELISA reader.

V3-loop binding assay

To investigate whether the epitope of S1-1 exists within the V3-loop on gp120, the binding of S1-1 to a V3-loop peptide was examined by dot blot assay. One microgram of HIV/IIIB synthetic peptide (provided to the AIDS Research and Reference Reagent Program by Dr. Mark E. Gurney) was placed onto a nitrocellulose membrane in a Bio-Dot blotting apparatus (Bio-Rad). The nitrocellulose membrane was then blocked with 5% goat milk in PBS-Tween (0.05% Tween-20) at 4° C. overnight. Individual blots were incubated with S1-1, HIVIG, or an anti-IIIB-V3-loop mouse monoclonal antibody (DuPont, Cat#NEA-9305), at a concentration of 1 µg/ml for 1 hour and then washed with PBS-Tween. Alkaline phosphatase conjugated goat anti-human or goat anti-mouse IgG (Tago) was incubated with the blots for 1 hour on a rocker and then washed free of second antibody as above. Bromochloroindolyl phosphate (BCIP) (0.17%) and nitro blue tetrazolium (NBT) (0.34%) in carbonate buffer (pH 9.6) were used as a substrate for alkaline phosphatase. The alkaline phosphatase buffer was added to the blots and the NBT was allowed to precipitate onto the dots.

GR120-soluble CD4 inhibition assay

A 96-well microtiter ELISA plate was coated with 50 µl of soluble CD4 (sCD4) (Repligen) at 2 µg/ml and then blocked with 0.1% gelatin in PBS-Tween for 1 hour at 37° C. Ten-fold, serial dilutions of either HuMAb S1-1, F105 (provided by Dr. Marshall Posner, Brown University, Providence, RI) or a murine anti-V3-loop antibody (Dupont, IIIB sequence-specific) were pre-incubated with 2 µg/ml of recombinant gp120 (Repligen) for 1 hour at room temperature. The antibody-gp120 solution was then added to the sCD4 coated plate and incubated for 1 hour at room temperature. Then the plate was washed free of excess reagents with PBS-Tween and 50 µl of 0.5 µg/ml of biotinylated HIVIG was added to the plate and incubated as before. The plate was washed and streptavidin-alkaline phosphatase (Tago) was added. Finally, after 1 hour at room temperature the plate was washed free of excess reagent and 100 µl of p-nitrophenyl phosphate was added at 1 mg/ml in carbonate buffer, pH 9.6. The O.D. at 405 nm was quantitated on a Titertek multiskan ELISA reader.

RESULTS gp120-CD4 Inhibition ELISA Screening Method

A 96-well microtiter ELISA plate was coated with 50 µl of soluble CD4 (obtained from Repligen) at 4 µg/ml and then blocked with 0.1% gelatin in PBS-Tween for 1 hour at 37° C.

Ten-fold serial dilutions of antibody S1-1, F105 (provided by Dr. M. Posner, Brown University) or a murine anti-V3-loop antibody (Dupont, IIIb sequence specific) were preincubated with 0.125 µg/ml of recombinant gp120 (obtained from Repligen) for one hour at room temperature. The antibody-gp120 solution was then added to the sCD4 coated plate and incubated for one hour at room temperature. The plate was then washed free of excess reagents with PBS-Tween and 50 µl of 0.5 µg/ml of biotinylated pooled human anti-HIV was added to the plate and incubated as before. The plate was washed and streptavidin-alkaline phosphatase was added. Finally, after one hour at room temperature, the plate was washed free of excess reagent and 100 µl of p-nitrophenyl phosphate was added. The optical density at 405 nm was read on a Titertek-multiskan ELISA reader.

Figure 6:
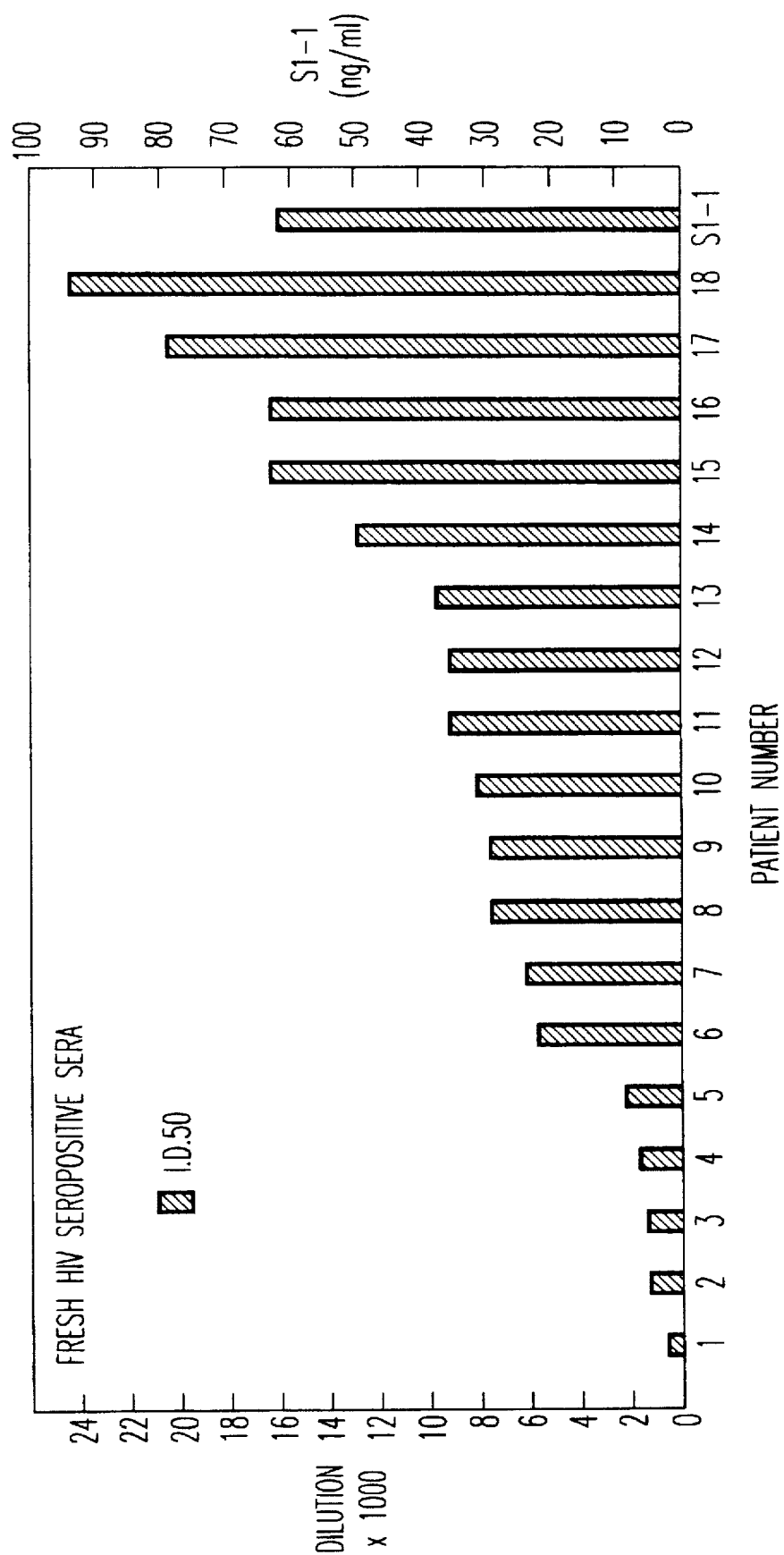
FIGS. 6 and 7 show the results of the gp120-CD4 inhibition assay/screening method of the present invention. This is a unique method which has not heretofore been reported to screen hybridomas for appropriate activity.

FIG. 6 shows the results of the gp120-CD4 inhibition ELISA screening method on recently collected sera from 18 patients. The fresh sera was collected from HIV patients who were in relatively good condition, i.e., either ARC or asymptomatic. Five of the 18 patients showed 50% inhibition of blocking (ID50) at greater than 1:10,000 dilution of serum. Monoclonal antibody S1-1 shows an ID50 concentration of 62 ng/ml.

Figure 7:
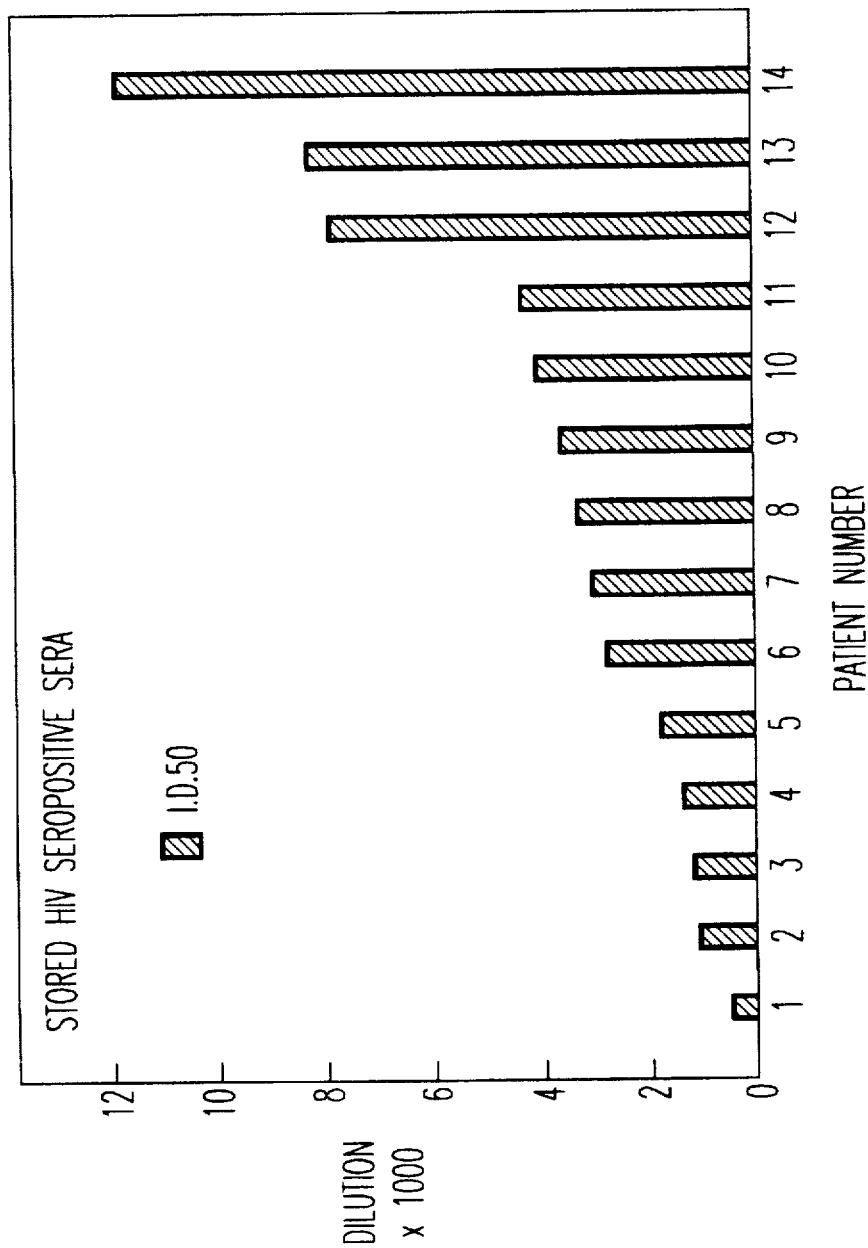
Figure 8A:
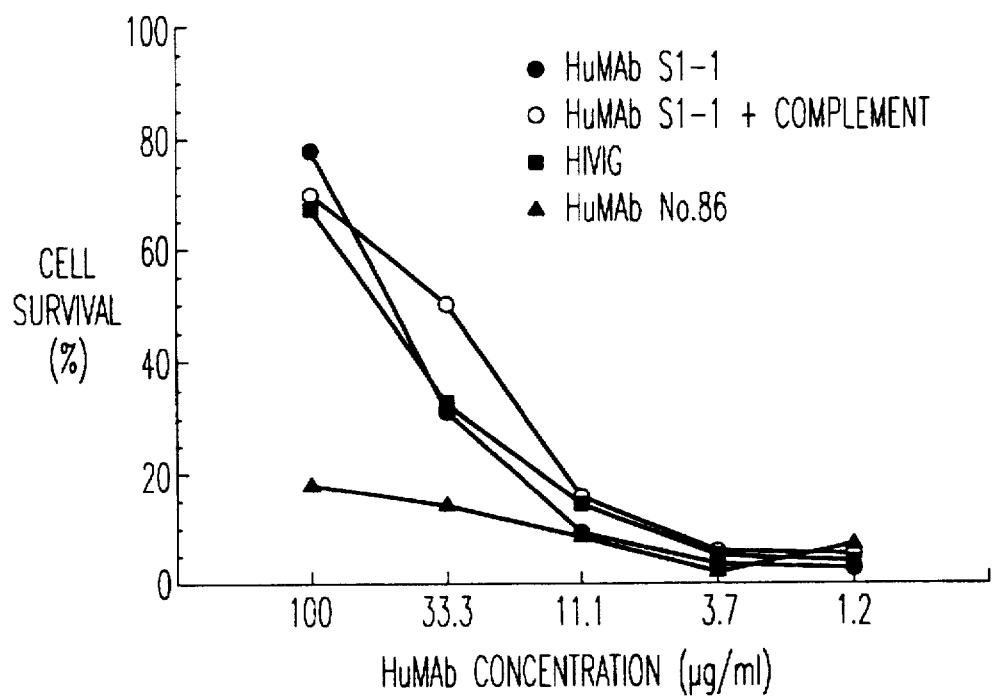
FIG. 8A: S1-1 neutralization of HIV/IIIB, maximal neutralization independent of complement occurred at 100 μg/ml, ID50 at 32 μg/ml of S1-1.
Figure 8B:
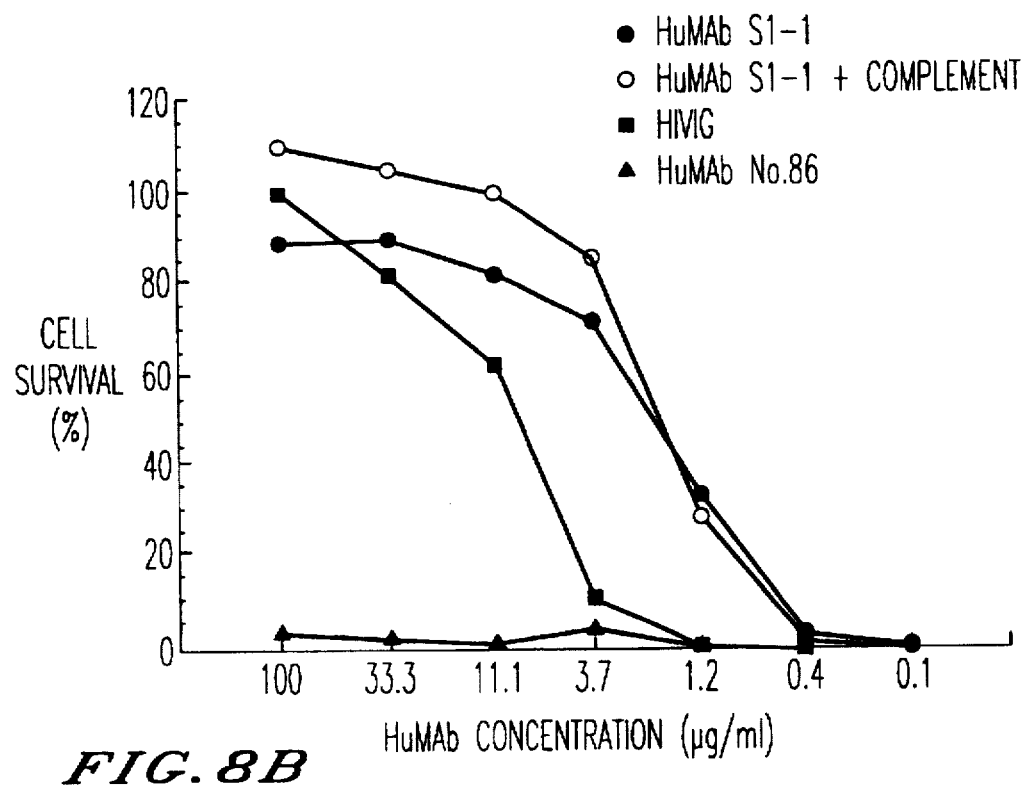
FIG. 8B: S1-1 neutralization of HIV/MN at ID50 of 2.0 μg/ml independent of complement.
Figure 8C:
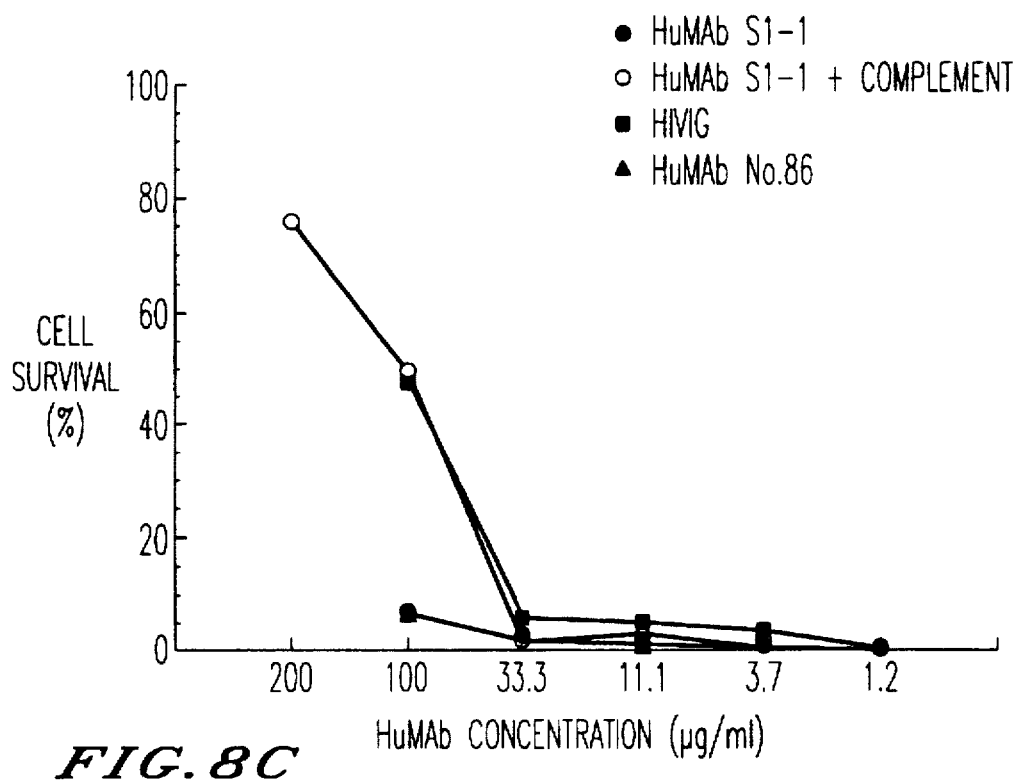
FIG. 8C: S1-1 complement-dependent neutralization of HIV/RF at ID50 of 100 μg/ml.
Figure 8D:
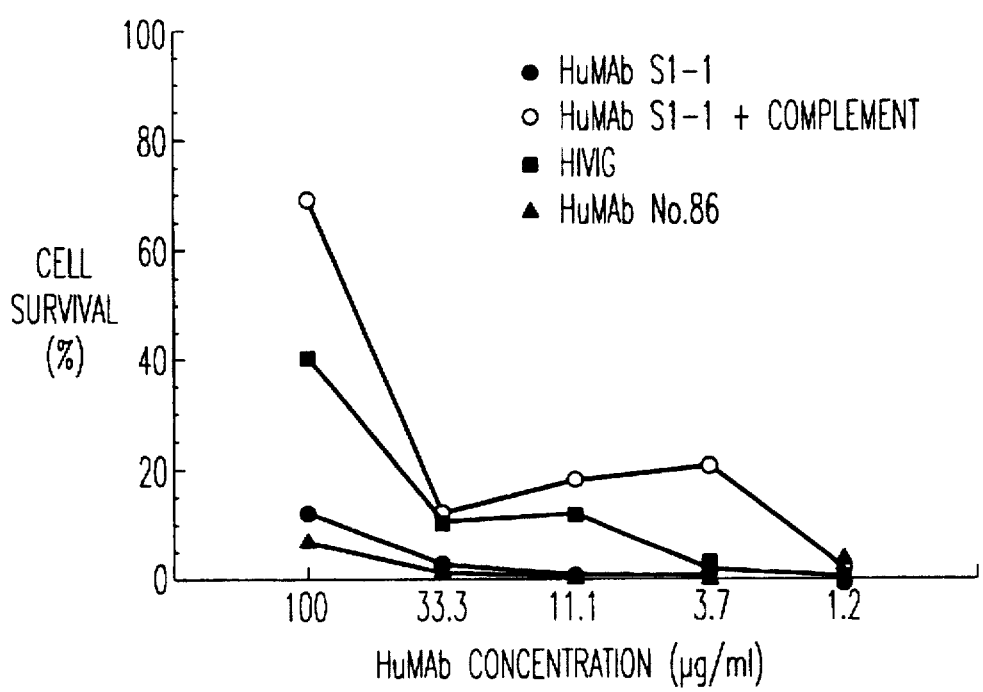
FIG. 8D: S1-1 complement-dependent neutralization of clinical isolate #20, maximal neutralization at 100 μg/ml at ID50 of 68 μg/ml of S1-1.

FIG. 7 shows the results on 14 patients with advanced disease whose sera had been stored frozen. The ID50 of two of these sera was at a dilution factor greater than 1:8,000 and one was greater than 1:10,000.

The results illustrated in FIGS. 6 and 7 show that a majority of HIV patient's sera show some degree of blocking of gp120/CD4 binding. Even sera from patients with advanced disease shows a substantial degree of blocking. These data indicate that the screening method of the present invention is suitable for identifying donors with very high titer blocking antibody as suitable sources for B-lymphocytes.

Neutralization assay

S1-1 neutralized HIV/IIIB and MN independent of complement and neutralized the divergent isolate, HIV/RF along with a clinical isolate #20, only in the presence of complement (FIG. 8). FIG. 8A shows complement-independent neutralization of HIV/IIIB. The ID50 (inhibitory dose in which 50% of the lytic effects of HIV were inhibited by antibody) of S1-1 in the presence and absence of complement was 32 µg/ml and 40 µg/ml, respectively for HIV/IIIB. FIG. 8B also shows complement-independent neutralization by S1-1 of HIV/MN. S1-1 was able to strongly neutralize HIV/MN with an ID50 of 2.0 µg/ml. In FIG. 8C, S1-1 neutralized the HIV/RF isolate only in the presence of complement; the ID50 was 100 µg/ml. In FIG. 8D, S1-1 neutralized clinical isolate #20 only in the presence of complement with an ID50 of 68 µg/ml. At varying degrees of neutralization, HIVIG neutralized all HIV strains tested, while an anti-gp41 HuMAb, No. 86, did not neutralize any of the strains tested. In other experiments S1-1 neutralized HIV/IIIB and MN using MT-2 cells, another CD4+ cell line, at concentrations similar to those shown for MoT cells.

Flow cytometry

In flow cytometric analysis, S1-1 reacted with the surface of HIV/IIIB and HIV/RF infected MoT cells and HIV/MN-infected H9 cells (FIG. 9B).

Western blot analysis

S1-1 did not bind to SDS-PAGE denatured HIV antigens in a Western blotting format.

Radioimmunoprecipitation assay (RIPA)

Upon incubation of S1-1 with $^{35}$S-Methione/Cysteine-labeled HIV/IIIB, MN and RF cell free virus, S1-1 reacted with gp120 from these three diverse isolates, confirming the broad specificity observed with S1-1 in flow cytometry.

Since S1-1 did not bind to denatured antigens in Western blotting, an experiment was run to determine if the epitope of S1-1 was disulfide bond-dependent. In RIPA using lentil lectin-purified HIV/IIIB-infected cell lysates, S1-1 bound to non-reduced gp120 and gp160. Upon treatment of the HIV-infected cell lysate with 5 mM DTT, S1-1 no longer recognized gp160 and gp120. When HIVIG was incubated with DTT-treated HIV-infected cell lysate, HIVIG did not recognize gp120 but retained the ability to recognize gp160. Upon subsequent titration of DTT, approximately 90% of HuMAb S1-1 and HIVIG reactivity with gp120 was lost at only 1 mM DTT and 5 mM, respectively.

V3-loop binding assay

S1-1 did not bind to a V3-loop peptide from HIV/IIIB blotted onto nitrocellulose membrane (the IIIB strain was neutralized by S1-1). In contrast, the anti-HIV/IIIB V3-loop mouse monoclonal antibody bound to the peptide very strongly, whereas HIVIG bound to the V3-loop less strongly at the same antibody concentration.

GP120-soluble CD4 inhibition assay

It has been reported by Ho et al (J. Virol., 65:489–493, 1991) that a broadly neutralizing anti-HIV human monoclonal antibody (15e) completely inhibited soluble CD4 (sCD4) from binding to gp120. We performed a similar gp120-sCD4 inhibition assay to determine whether S1-1 inhibited the binding of gp120 to sCD4. The results showed that S1-1 inhibited gp120 from binding to sCD4 at concentrations as low as 10 μg/ml. HuMAb F105 effectively inhibited gp120 from binding to sCD4 at concentrations of about 10 μg/ml. In contrast, an anti-V3-loop neutralizing antibody, which binds to the gp120 used in this experiment, did not inhibit the binding of gp120 to sCD4 at any of the concentrations tested.

These results indicate that S1-1 does not bind to the V3-loop on gp120, but does bind to gp120 in or near the CD4 binding site. S1-1 inhibits infection of cells by a variety of HIV isolates indicating a group-specific epitope. The results discussed above and the observation that S1-1 effectively inhibits the binding of gp120-sCD4 in ELISA strongly indicate that S1-1 neutralizes HIV by blocking the gp120-CD4 interaction, which has been found to be critical for HIV infectivity.

The human monoclonal antibody 15e of Ho et al has been found to effectively inhibit sCD4 from binding to gp120, neutralized multiple HIV isolates, but did not neutralize the HIV/RF isolate. In contrast, antibody S1-1 did not bind to denatured gp120 in Western blotting or to DTT-reduced gp120 in RIPA, but neutralized HIV/RF in the presence of complement.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for neutralizing a human immunodeficiency virus type 1 (HIV-1), comprising:

contacting an HIV-1 with human monoclonal IgG1 antibodies produced by hybridoma ATCC Accession No. HB10074 which immunologically bind to gp120 glycoprotein on the surface of said HIV-1 and prevent binding of gp120 glycoprotein to lymphocyte CD4.

2. The method of claim 1, wherein said antibodies are produced by a subcloned cell line obtained from hybridoma ATCC Accession No. HB10074 by limiting dilution.

* * * * *